United States Patent
Takeuchi et al.

(10) Patent No.: US 8,105,691 B2
(45) Date of Patent: Jan. 31, 2012

(54) HYDROPHILIZED SURFACE-TREATED POWDER AND COSMETICS CONTAINING SAME

(75) Inventors: Yasushi Takeuchi, Saitama (JP); Shinya Kuwazuru, Saitama (JP); Masaakira Horino, Kanagawa (JP)

(73) Assignee: Miyoshi Kasei, Inc., Saitama-shi, Saitama (JP)

( * ) Notice: Subject to any disclaimer, the term of this patent is extended or adjusted under 35 U.S.C. 154(b) by 51 days.

(21) Appl. No.: 11/995,617

(22) PCT Filed: Jun. 21, 2006

(86) PCT No.: PCT/JP2006/312388
§ 371 (c)(1),
(2), (4) Date: Jun. 3, 2009

(87) PCT Pub. No.: WO2007/007521
PCT Pub. Date: Jan. 18, 2007

(65) Prior Publication Data
US 2009/0263660 A1    Oct. 22, 2009

(30) Foreign Application Priority Data

Jul. 13, 2005   (WO) ............... PCT/JP2005/012928

(51) Int. Cl.
*B32B 5/16* (2006.01)
(52) U.S. Cl. ........ 428/407; 424/401; 424/475; 424/476; 424/480; 424/490; 424/494; 424/497; 424/498; 428/403
(58) Field of Classification Search ............... 428/402, 428/403; 424/401, 475, 476, 480, 490, 494, 424/497, 498
See application file for complete search history.

(56) References Cited

U.S. PATENT DOCUMENTS

| | | | |
|---|---|---|---|
| 5,034,476 A | | 7/1991 | Saito et al. |
| 5,468,474 A | * | 11/1995 | Honda et al. ............... 424/70.1 |
| 5,922,357 A | | 7/1999 | Coombes et al. |
| 5,977,229 A | | 11/1999 | Barth et al. |
| 6,001,378 A | * | 12/1999 | Desjonqueres ............... 424/401 |
| 2003/0108501 A1 | * | 6/2003 | Hofrichter et al. ........... 424/70.1 |
| 2004/0091440 A1 | * | 5/2004 | Kamei ....................... 424/70.12 |
| 2004/0253284 A1 | * | 12/2004 | Horino et al. ............... 424/401 |
| 2005/0169867 A1 | | 8/2005 | Horino et al. |
| 2005/0196363 A1 | | 9/2005 | Horino |
| 2006/0177395 A1 | * | 8/2006 | Candau ......................... 424/59 |

FOREIGN PATENT DOCUMENTS

| | | |
|---|---|---|
| JP | 61-286310 A | 12/1986 |
| JP | 63-57516 A | 3/1988 |
| JP | 1-266141 A | 10/1989 |
| JP | 1-301760 A | 12/1989 |
| JP | 02-9811 A | 1/1990 |
| JP | 3-294220 A | 12/1991 |
| JP | 9-104833 A | 4/1997 |
| JP | 9-110642 A | 4/1997 |
| JP | 9-124855 A | 5/1997 |
| JP | 9-511002 A | 11/1997 |
| JP | 2001-114649 A | 4/2001 |
| JP | 2001-220319 A | 8/2001 |
| JP | 2003-26958 A | 1/2003 |
| JP | 2005-213362 A | 8/2005 |
| JP | 2005-247720 A | 9/2005 |

OTHER PUBLICATIONS

International Search Report of PCT/JP2006/312388, date of mailing Sep. 19, 2006.
English translation of PCT/JP2006/312388 Preliminary Report on Patentability (Forms PCT/IB/338, PCT/IB/373 and PCT/ISA/237).

* cited by examiner

*Primary Examiner* — Hoa (Holly) Le
*Assistant Examiner* — Ronak Patel
(74) *Attorney, Agent, or Firm* — Westerman, Hattori, Daniels & Adrian, LLP

(57) ABSTRACT

By coating the surface of a powder comprising a silicone resin and/or an organic powder with a specific hydrophilizing agent, such powder is hydrophilized. Such coated (treated) powder has extremely great dispersibility (ease of dispersion) and very good dispersion stability (long-term dispersion stability with lapse of time) in aqueous dispersion media, particularly under acidic and alkaline conditions, specifically at pH 3 through 13. Using the surface-treated powder, additionally, a dispersion with good dispersibility (ease of dispersion) and great dispersion stability, preferably for cosmetics can be provided. The use of the surface-treated powder, or the use of the dispersion can provide further a cosmetic excellent in dispersibility and dispersion stability and further in re-dispersibility and dispersion stability with lapse of time and smooth feeling as compared to the related art when selecting aqueous cosmetic as an agent form.

10 Claims, No Drawings

HYDROPHILIZED SURFACE-TREATED POWDER AND COSMETICS CONTAINING SAME

TECHNICAL FIELD

This application is based upon and claims the benefit of the priority from International Application No. PCT/JP2005/012928 filed on Jul. 13, 2005, the disclosure of which is incorporated herein in its entirety by reference.

The present invention relates to a surface-treated powder, more specifically to a novel surface-treated powder prepared by treating (coating) the surface of a powder (particle) comprising a silicone resin and/or an organic powder (at least one selected from PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of one or more of these organic powders with a metal oxide and/or a metal hydroxide) with a specific hydrophilizing agent (surface-treating agent), such as a water-soluble polyoxyalkylene glycol derivative, as well as a dispersion and a cosmetic containing the same.

In accordance with the invention, the agglomeration (aggregation) of a powder (a silicone resin and/or an organic powder) to be incorporated (blended) in aqueous dispersant media (dispersion medium of aqueous type) and cosmetics, particularly under acidic and alkaline conditions, specifically at pH 3 to 13 can be suppressed to uniformly disperse the powder in the aqueous dispersion media and the cosmetics and maintain the dispersed state for a long period of time. Such cosmetics are quite excellent in smooth (application) feeling such as moist (dewy) touch.

Furthermore, the surface-treated powder of the invention and the dispersion of the invention can preferably be used as a surface-treated powder for cosmetics and a dispersion for cosmetics and additionally, as well as cosmetics the surface-treated powder and the dispersion may be applied to various fields of additives for plastic products such as plastic films and plastic sponges; dispersion aids for inks, de-lustering paints, toners (magnetic powders), synthetic resins, rubbers, silicones, chemical fibers, materials for packaging, electronic materials, liquid crystal-related materials, pigments and ceramics; solidification inhibitors, and optical diffusing agents blocking inhibitors or anti-slip agents for information-recording paper and the like.

BACKGROUND OF THE INVENTION

Cosmetics contain powders or pigments for improving coloration, feeling and the like. In case that powders and pigments are to be used for these purposes, it is required that the powders and pigments should be uniformly dispersed in cosmetics (cosmetic compositions) to obtain cosmetics having high long-term dispersion stability without unevenness in color and the like. However, in case that ordinary powders or pigments are selected to be dispersed in aqueous dispersion media, there is a need to hydrophilize (make a hydrophilic treatment) them. Without hydrophilization (hydrophilic treatment), depending on the selection of various agent form, it is impossible to obtain cosmetics having good dispersibility and long-term dispersion stability and further having, when selecting aqueous cosmetics (cosmetics of aqueous type) as the agent form thereof, ready re-dispersibility (ease of re-dispersion) and long-term dispersion stability with lapse of time.

Alternatively, many proposals have been so far made for hydrophilicaly treating hydrophobic powders or pigments (refer to Patent Documents 1 to 5).

It is reported that in case of for example a dispersion prepared by dispersing a pigment excellent in water resistance and weatherability (weather resistance) into water using a surfactant, the pigment is stably dispersed in water by the surfactant, so that the pigment remains dispersed in a stable manner and does not precipitate in the system for a certain length of time (refer to Patent Document 1).

Furthermore, it is reported that an inorganic pigment hydrophilicaly treated (hydrophilized) by coating the inorganic pigment with a water-soluble polymer has good dispersibility in water and stable dispersibility (refer to Patent Document 2).

Still further, a pigment treated hydrophilicaly by coating the pigment with a nonionic surfactant of HLB 7 to 18 and a fatty acid soap has good dispersibility in water without any occurrence of precipitation or adhesion, even after use for a long period of time (refer to Patent Document 3).

However, the method of hydrophilic treatment (surface treatment) with the surfactant or the water-soluble polymer or the combination of the nonionic surfactant and the fatty acid soap is said to be hard in being satisfactory for dispersing hydrophobic powders or pigments in an aqueous dispersion medium. When the hydrophilicaly treated (hydrophilicaly-treated) powder is incorporated into cosmetics therewith, the powders or the pigments are dissociated or separated in the system, so that the powders or the pigments agglomerate. Consequently, this causes uneven color or a difference between color in appearance and color at the time of application therein or long-term dispersion stability with lapse of time is impaired, or in case of some form of cosmetics, the re-dispersibility of the powders or the pigments in the system may be worsened to cause caking and notably decreases its usability.

From the standpoints of heat resistance, water resistance, refractive index, coloration and the like, cosmetics contain, as a powder for cosmetics, a silicone resin or an organic powder (PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of one or more of these organic powders with a metal oxide and/or a metal hydroxide) are blended as cosmetic powders in the cosmetics. It is very hard to disperse these powders (particles) in an aqueous dispersion medium by hitherto-proposed methods for hydrophilicaly treating hydrophobic powders or pigments.

For example, a powder which is hydrophilicaly treated with a silylating agent having a polyethylene chain is proposed, and it is reported that in case that this powder is incorporated into a nail enamel of an aqueous type along with an acrylic type polymer emulsion, a nail enamel of an aqueous type which is excellent in dispersion stability of a powder can be provided (refer to Patent Document 4).

Additionally, a hydrophilicaly treated pigment, in which a hydrophilic organic group is introduced into a pigment using a hydrophilic silane compound or silane coupling agent, and a composition containing the same is proposed (refer to Patent Document 5).

However, a pigment that is hydrophilicaly surface treated with polyethylene chain having a silylating agent is incorporated along with the above mentioned acrylic type polymer emulsion, and the above-mentioned hydrophilicaly surface treated pigment in which the hydrophilic organic group is introduced with the hydrophilic silane compound or silane coupling agent, do not satisfy the dispersibility or the long-term dispersion stability in various cosmetics systems. Accordingly, even when using a silicone resin and an organic powder with a strong hydrophilic property, the dispersibility in the system of the cosmetics and the long-term dispersion stability can not be satisfactory. The refractive index, transparency, the lubricity, the elasticity, the touch and the like which are effects provided by the silicone resin and the organic powder can hardly be exerted sufficiently.

In make-up cosmetics containing powders, for example, a cake type foundation, a humectant has been used to impart a moist feel for a smooth feeling, especially a smooth feeling after use to the skin. When cosmetics containing a humectant are applied on the skin, however, since the oil absorption or water absorption of the powder is too strong, the powder adsorbs the sebum or moisture, more than as required, from the skin. In other words, cosmetics containing a humectant lack a smooth feeling, especially a moist touch, and the use of a humectant in cosmetics causes an increase in a rough feeling or a dry feeling of the skin. When such cosmetics are applied on the skin, therefore, it provides a hard feeling to skin, but not a soft feeling. In addition, affixture of a powder contained in cosmetics to the skin is worsened, and adhesion of a cosmetic film on the skin is deficient. As the results of these, consequently, these defects have also caused the makeup to come off. Particularly, the rough feeling of the skin has been clearly problematic in winter.

In order to solve this problem, the addition of a humectant such as glycerin, propylene glycol or 1,3-butylene glycol to cosmetics has been attempted so far. When cosmetics containing a powder are produced by simply mixing a humectant with other ingredients, various ingredients are used as starting materials for cosmetics to be adhered to or adsorbed on the surface of the powder, and further the surface properties of the powder become heterogeneous, and the affixture to the skin decreases. Consequently, the rough feeling and the dry feeling of the skin cannot be improved, and the makeup is liable to come off due to secretion from the skin, the movement of muscles of facial expression, and the like. In addition, when the humectant is incorporated (mixed) along with the powder, the low-molecular part of the humectant is adsorbed on the powder, but the majority of the humectant is easily desorbed from the surface of the powder, so that a mere wetting phenomenon is shown. Thus, the humectant does not basically change the surface properties of the powder. Accordingly, it is impossible to decrease the rough feeling on the skin caused by the powder and improve the affixture to the skin, so that the moist touch cannot be improved and maintained. Moreover, the unevenness of the cosmetic film caused by the powder formed on the skin cannot basically be eliminated, thereby contributing to the makeup coming off the skin.

There is also a method in which affinity for water in a powder is increased by treating the powder with silica and alumina. However this method has been problematic in that the surface activity of the powder does not have sufficient dispersibility in water. Furthermore, in cosmetics containing the treated powder (silica- or alumina-treated powder), the powder itself and the surface-treating agent applied to its surface become separated or dissociated. Consequently, the powder aggregates in the system, or thereby a difference between the appearance color and application color is caused.

In addition, depending on the different form of cosmetics, for example, in case of a cosmetic of bi-layer type, the powder might cause a caking phenomenon to notably decrease re-dispersibility and greatly impair usability.

In most of the methods for hydrophilicaly treating hydrophobic powders or pigments, which have been so far proposed, for example, by reason that a coated film on the powder is dissolved in an aqueous dispersion medium or cosmetics under acidic and alkaline conditions, especially in alkaline conditions, it is difficult to uniformly disperse the powder in the aqueous dispersion medium or cosmetics and maintain this dispersed state for a long period of time (refer to Patent Documents 6 to 8).

For example, a coated pigment is proposed in which a surface of an inorganic pigment is coated with a polyvalent metal salt of an anionic high-molecular compound, and it is reported that a makeup product containing the same, is excellent in its affixture to the skin and the like (refer to Patent Document 6).

A water-dispersible pigment is proposed in which a pigment powder (an inorganic pigment, an organic pigment, carbon or a resin powder pigment) is surface-treated with a specific alkoxysilane compound, and it is reported that such a pigment is easily dispersed in neutral water and is excellent in water dispersion stability over a long period of time and coating stability (refer to Patent Document 7).

Still additionally, a hydrophilicaly modified polyethylene of a high molecular weight is proposed, as prepared by treating a high-molecular polyethylene with a mixture of a water-soluble surfactant and a water-insoluble polyalkylene glycol. It is reported that such polyethylene has great stability for a long period of time and temperature-stability (refer to Patent Document 8).

Nevertheless, in the pigment coated with the polyvalent metal salt of the anionic high-molecular compound, the above water-dispersible pigment surface-treated with the specific alkoxysilane compound, and the polyethylene with the surface treated with a mixture of a water-soluble detergent and a water-insoluble polyalkylene glycol, the coated films on their surface are dissolved under alkaline conditions. Therefore, in cosmetics containing these hydrophilicaly treated pigments, similar to the above, for example, the pigments may be dissociated or separated in the system, and subsequently aggregated, and consequently create an uneven color or difference in color between appearance and at the time of application, or long-term dispersion stability with lapse of time may be impaired.

Accordingly, in a system in which the cosmetics (especially cosmetics of aqueous type) contain a surface-treated powder hydrophilicaly treated by the above conventional method of hydrophilic treatment, the surface-treated powder hydrophilicaly treated by the above conventional method of hydrophilic treatment aggregates, or the dispersion stability with lapse of time is impaired. Thus, the effects thereof are hardly exhibited satisfactorily. Especially, in most of surface-treated powders which are hydrophilicaly treated by the above conventional methods of hydrophilic treatment, the coated film of the powder is dissolved under alkaline conditions. Therefore, these problems are clearly seen in the system in which the powder is incorporated in alkaline cosmetics. Accordingly, it is desirable to develop a powder obtained (prepared) by hydrophilicaly treating the silicone resin and/or the organic powder (PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of one or more of these organic powders described above with a metal oxide and/or a metal hydroxide) (particle), especially in which the coated film of the powder is not dissolved even under alkaline conditions, preferably for cosmetics. Additionally, no description is found with respect to a surface-treated powder which is prepared by hydrophilicaly treating the silicone resin or the organic powder (particle) by hydrophilic treatment, of which the coated film is not dissolved even under acidic and alkaline conditions and which is excellent in dispersibility and long-term dispersion stability, a dispersion and cosmetics containing the same, and the like.

Patent Document 1: Japanese Patent Kokai Publication JP-A-1-301760

Patent Document 2: Japanese Patent Kokai Publication JP-A-63-57516

Patent Document 3: Japanese Patent Kokai Publication JP-A-3-294220

Patent Document 4: Japanese Patent Kokai Publication JP-A-9-110642

Patent Document 5: Japanese Patent Kokai Publication JP-A-9-104833

Patent Document 6: Japanese Patent Kokai Publication JP-A-61-286310

Patent Document 7: Japanese Patent Kokai Publication JP-A-2003-26958

Patent Document 8: Japanese Patent Kokai Publication JP-A-9-124855

DISCLOSURE OF THE INVENTION

Problems that the Invention is to Solve

The disclosures of the above-mentioned Patent Documents 1 to 8 are herein incorporated by reference thereto.

The following analysis is given by the present invention.

Under these circumstances, it is desirable to develop a surface-treated powder, especially a surface-treated powder for cosmetics, which has satisfactory hydrophilic property and is excellent in dispersibility (ease of dispersion) in an aqueous dispersion medium and long-term dispersion stability (stability with lapse of time) as never found in the related art even when being incorporated into an aqueous dispersion medium or cosmetics in acidic and alkali conditions, specifically at pH 3 through 13, a dispersion which contains the same, and is excellent in dispersibility and long-term dispersion stability, and a cosmetic which contain the same and is excellent in dispersibility, long-term dispersion stability, and smooth feeling (especially moist touch), also excellent in persistence of such a smooth feeling and further excellent in ready re-dispersibility (ease of re-dispersion) and long-term dispersion stability with lapse of time in case of selecting an aqueous cosmetic (cosmetic of aqueous type) as an agent form. Herein, the present applicant has filed the application relating to a novel surface-treated powder in which a surface of particles of a pigment powder is treated (coated) with a low-molecular organosilicon derivative, with or without a water-soluble cationic polymer (refer to Japanese Patent Application No. 2004-021659 and the Japanese Patent Application No. 2004-057674). These surface-treated powders exert great dispersibility (ease of dispersion) in an aqueous dispersion medium and also has excellent long-term dispersion stability (stability with lapse of time) as never found in the related art even when the powders are incorporated into an aqueous dispersion medium or cosmetics under acidic and alkaline conditions, specifically at pH 3 to 13. The powders may be dispersed uniformly in an aqueous dispersion medium or cosmetics. However, further improvement is demanded to allow the dispersion state to be maintained for a longer time. Therefore, it is an object of the invention to provide a surface-treated powder, which has satisfactory hydrophilic property and is excellent in dispersibility (ease of dispersion) in an aqueous dispersion medium and particularly excellent in long-term dispersion stability (stability with lapse of time) when being incorporated into an aqueous dispersion medium or cosmetics in acidic and alkali conditions, specifically at pH 3 through 13, a dispersion which contains the same, and is excellent in dispersibility and long-term dispersion stability, and a cosmetic which contain the same and is excellent in dispersibility, long-term dispersion stability, and smooth feeling (especially moist touch), also excellent in persistence of such a smooth feeling, and particularly excellent in long-term dispersion stability and further excellent in ready re-dispersibility (ease of re-dispersion) and long-term dispersion stability with lapse of time in case of selecting an aqueous cosmetic (cosmetic of aqueous type) as an agent form.

Means for Solving the Problems

As a result of perseverant researches towards the hydrophilic treatment of powders (particles) comprising a silicone resin and/or an organic powder (PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of one or more of these organic powders described above with a metal oxide and/or a metal hydroxide) as the powder to be surface-treated, the present inventors have found that, in case that at least one of the powders to be surface-treated is surface-treated (coated) with specific hydrophilizing agent(s), specifically water-soluble polyoxyalkylene glycol derivative(s), particularly hydrophilizing agent(s) containing the water-soluble polyoxyalkylene glycol derivative(s) with water-soluble cationic polymer(s), or hydrophilizing agent(s) containing the water-soluble polyoxyalkylene glycol derivative(s) with water-soluble cationic polymer(s) and low-molecular organosilicon derivative(s), by a kneading process with a kneading apparatus in particular, the gelation reaction of the hydrophilizing agent progresses on the particle of the powder to be surface-treated, so that a strongly coated film never dissolvable under acidic and alkaline conditions is formed. The inventors have found that because the coated film on the surface-treated powder obtained in such manner is not dissolved in an aqueous dispersion medium or cosmetics, especially an aqueous dispersion medium or cosmetics in acidic and alkaline conditions, specifically with pH between 3 to 13, so that the powder is uniformly dispersed in the aqueous dispersion medium or the cosmetics, the hydrophilicity is especially maintained for a long period of time and the dispersed state is also maintained for a long period of time.

It has been further found that when the surface-treated powder is incorporated in the aqueous dispersion medium, the dispersion quite excellent in dispersibility and especially long-term dispersion stability can be produced, and that the cosmetics containing the surface-treated powder as a powder or the dispersion containing the same are quite excellent in ready re-dispersibility and long-term dispersion stability with lapse of time, impart an excellent smooth feeling, especially a moist touch to the skin and are also excellent in persistence thereof. These findings have led to the completion of the present invention.

That is, the present invention lies in a surface-treated powder prepared (obtained) by coating the surface of a powder comprising a silicone resin and/or an organic powder with a hydrophilizing agent (hereinafter also referred to as "the surface-treated powder of the present invention"), wherein the hydrophilizing agent is a water-soluble polyoxyalkylene glycol derivative and the organic powder is at least one selected from PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of one or more of these organic powders described above with a metal oxide and/or a metal hydroxide.

In the present invention, the hydrophilizing agent additionally contains preferably a water-soluble cationic polymer, more preferably a water-soluble cationic polymer and a low-molecular organosilicon derivative. Herein, the particle diameter of the particle of the powder to be surface-treated may be 0.01 to 100 μm as the mean particle diameter.

In the present invention, further, polymethylsilsesquioxane can be selected as the silicone resin; as the water-soluble polyoxyalkylene glycol derivative, there can be selected at least one of polyoxyethylene monoester, polypropylene glycol monoester, polyoxyethylene glyceryl fatty acid, and polyoxyethylene glyceryl isostearate; as the water-soluble cationic polymer, there can be selected at least one of dimethyldiallylammonium chloride-acrylamide copolymer, polydimethylmethylene piperidinium chloride, and o-[2-hydroxy-3-(trimethylammonio)propyl]hydroxyethylcellulose chloride; and as the low-molecular organosilicon derivative, there can be selected at least one of dimethylsilanediol hyaluronate, monomethylsilanetriol lactate, methylsilanol mannuronate, and methylsilanol triPEG-8-glyceryl cocoate.

The surface of the particle of the powder comprising the silicone resin and/or the organic powder is coated with the hydrophilizing agent, so as to coat 0.01 to 50% by weight of the surface of the particle of the powder comprising the silicone resin and/or the organic powder.

In another example, the present invention lies in a dispersion, preferably a dispersion for cosmetics (hereinafter also referred to as "the dispersion of the present invention") which comprises the surface-treated powder described above.

In still another example, the present invention lies in a cosmetic (hereinafter also referred to as "the cosmetic of the present invention") which comprises the surface-treated powder described above.

As the agent form of the cosmetic of the present invention, any one of aqueous products, emulsified products, oily products, powdery products, aerosol products, solid products and tablet products can be selected. Particularly, any one of rinsing cosmetics, skincare cosmetics, make-up cosmetics, haircare products, deodorizing products, dental paste, bath products, aromatic products, anti-perspiration cosmetics, and anti-ultraviolet cosmetics is preferably selected.

Effect of the Invention

The meritorious effects of the present invention are summarized as follows.

In accordance with the present invention, a surface-treated powder (a surface-treated powder for cosmetics, in particular) can be provided, which is easily dispersed uniformly in the aqueous dispersion medium, especially the aqueous dispersion medium in acidic and alkaline conditions, specifically with pH between 3 to 13, for a long period of time. Additionally, a dispersion (a dispersion for cosmetics in particular), containing (dispersing) the surface-treated powder in water or a water-soluble solvent or a mixture thereof, with quite excellent in dispersibility (ease of dispersion) and particularly long-term dispersion stability can be also provided.

Further, using said surface-treated powder or said dispersion, a cosmetic with excellent dispersibility and long-term dispersion stability and further, in case of selecting aqueous cosmetic, excellent ready re-dispersibility and long-term dispersion stability with lapse of time and superior smooth feeling such as moist touch and the like can be produced simply. Therefore, the present invention is especially useful in a cosmetic industry.

PREFERRED MODE FOR CARRYING OUT THE INVENTION

The preferred mode for carrying out the invention is now described hereinbelow, with attention focused on a surface-treated powder prepared by coating the surface of a powder comprising a silicone resin and/or an organic powder (at least one selected from PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite (particle) of one or more of these organic powders described above with a metal oxide and/or a metal hydroxide) with a hydrophilizing agent, specifically a water-soluble polyoxyalkylene glycol derivative, particularly a hydrophilizing agent containing the water-soluble polyoxyalkylene glycol derivative with a water-soluble cationic polymer, or a hydrophilizing agent containing the water-soluble polyoxyalkylene glycol derivative with a water-soluble cationic polymer and a low-molecular organosilicon derivative, namely the surface-treated powder of the invention. However, the present invention is not limited thereto. In accordance with the invention, herein, "the silicone resin and/or the organic powder" may be in the form of either a powder or particles.

(The Surface-treated Powder of the Invention)

The surface-treated powder of the present invention is preferably a surface-treated powder for cosmetics, wherein the powder to be surface-treated (the powder before the surface treatment) comprises a silicone resin and/or an organic powder. Additionally, the organic powder is at least one selected from PMMA, nylon, polyester, polystyrene, cellulose, silicone elastomer powder (dimethicone-crosslinked elastomer), silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite (particle) of at least one of these organic powders described above with a metal oxide and/or a metal hydroxide. At least one selected from the group of these organic powders and elastomers, vinyl resins, urea resins, phenol resins, fluorine resins, silicon resins, acryl resins, melamine resins, epoxy resins, polycarbonate resins, microfine crystalline fiber powders, and metal soaps, and composites (particles) of one or more thereof with metal oxides and/or metal hydroxides may satisfactorily be selected. The N-acylated lysine preferably has at least one aliphatic acyl group with 8 to 22 carbon atoms within the molecule. The N-acylated lysine includes for example N-lauroyl lysine, N-myristyl lysine, N-stearyl lysine, and N-behenyl lysine. Among them, N-lauroyl lysine is particularly preferable because it can give excellent touch (or feeling) to the resulting cosmetics. The surface of the particle of the powder to be surface-treated is coated with a water-soluble polyoxyalkylene glycol derivative as a hydrophilizing agent, preferably a hydrophilizing agent containing a water-soluble polyoxyalkylene glycol derivative with a water-soluble cationic polymer, more preferably a hydrophilizing agent containing a water-soluble polyoxyalkylene glycol derivative with a water-soluble cationic polymer and a low-molecular organosilicon derivative.

There is no limitation to the silicone resin described above. For example, a silicone resin consisting of a combination of bifunctional silicone resin and trifunctional silicone resin, or a trifunctional silicone resin, or the like can be used. Preferably, a trifunctional silicone resin such as polymethylsilsesquioxane, especially preferably, polymethylsilsesquioxane is selected. The silicone resin described above is easily available. Silicone resins produced by a known method or purchased from a market (for example, trade name: TOSPEARL, manufactured by GE Toshiba Silicones, Ltd.) can be used.

Examples of the organic pigment described above include organic pigments such as red 201, red 202, red 204, red 205, red 220, red 226, red 228, red 405, orange 203, orange 204, yellow 205, yellow 401, and blue 404; organic lake pigments such as zirconium lakes, barium lakes, and aluminum lakes, for example red 3, red 104, red 106, red 227, red 230, red 401, red 505, orange 205, yellow 4, yellow 5, yellow 202, yellow 203, green 3, and blue 1; and natural dyes such as chlorophyll and β-carotene.

The composite pigment described above can include a composite obtained by combining at least one of PMMA, nylon, polyester, polystyrene, cellulose, silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, with a metal oxide such as silica, magnesia, alumina, calcium oxide, titanium oxide and iron oxide and/or a metal hydroxide such as iron hydroxide. Examples thereof include a nylon-silica composite, a nylon-magnesia composite, a nylon-alumina composite, a PMMA-alumina-magnesia composite, a nylon-iron oxide composite, a nylon-iron hydroxide composite, and a titanium oxide-red 226 composite.

Any silicone resin may be used as the silicone resin described above with no specific limitation. The composites of at least one of PMMA, nylon, polyester, polystyrene, cellulose, silicone elastomer powder (dimethicone-crosslinked elastomer), silicone elastomer powder, silicone rubber powder, benzoguanamine, styrenedivinylbenzene pinhole polymer, ethylene tetrafluoride, polyethylene powder, polypropylene powder, polyurethane powder, silk powder, metal soap powder, starch powder, N-acylated lysine, an organic pigment, and a composite of at least one of these organic powders described above with a metal oxide and/or a metal hydroxide are without any specific limitation. Thus, those produced by a known method or purchased from a market can be used. Additionally, these powders may or may not be preliminarily surface-treated by surface treatments known in the related art, for example, treatments with fluorine compounds, silicone treatments, treatments with silicone resins, pendant treatments, treatments with silane coupling agents, treatments with titanium coupling agents, treatments with oily agents, treatments with N-acylated lysine, treatments with polyacrylic acid, treatments with metal soaps, treatments with amino acids, treatments with lecithin, treatments with esters, treatments with inorganic compounds, plasma treatment and mechano-chemical treatments.

When surface-treated powders after surface-treatment with the hydrophilizing agent of for example various powders including for example inorganic powders, gloss powders, dye powders, metal powders and complex powders to be generally contained in cosmetics as colorants, screening agents, ultraviolet shielding agents, and providers of make-up effects, instead of the above powder used in the present invention, is dispersed in aqueous dispersion medium, the dispersion quite excellent in long-term dispersion stability and the like can be provided. Specifically, there can be selected powders such as white pigments including zinc oxide, titanium oxide, and cerium oxide; colored inorganic pigments including iron oxide, carbon black, chromium oxide, chromium hydroxide, Prussian blue, ultramarine blue, manganese violet, cobalt violet, cobalt oxide, and cobalt titanate; extender pigments such as talc, mica, white mica, gold mica, scarlet mica, black mica, synthetic mica, silk mica (selicite), synthetic selicite, kaolin, silicone carbide, silicic anhydride, aluminium oxide, magnesium oxide, zirconium oxide, antimony oxide, diatomaceous earth, aluminium silicate, magnesium aluminium metasilicate, calcium silicate, barium silicate, magnesium silicate, calcium carbonate, magnesium carbonate, hydroxyapatite, boron nitride, and barium sulfate; pearl pigments such as titanium oxide-coated mice, titanium oxide-coated bismuth oxychloride, iron oxide titanium mica, Prussian blue-treated titanium mica, carmine-treated titanium mica, bismuth oxychloride, and fish scale guanine; metal powders such as aluminium powder, gold powder, and silver powder; inorganic powders such as silica, alumina, magnesia and calcium oxide; and powders such as bentonite, smectite, and boron nitride. Furthermore, a cosmetic containing this coated product(s), or a dispersion is superior to ordinary products in dispersibility, long-term dispersion stability and the like.

The particle diameter of the powder before the surface treatment for use in accordance with the invention includes but is not limited to any particle diameter in smoke, microfine particles or pigment grades. The mean particle diameter is selected from preferably approximately 0.01 to 100 μm, more preferably approximately 0.01 to 50 μm, still more preferably approximately 0.01 to 30 μm, particularly preferably approximately 0.01 to 20 μm. It is difficult to prepare a powder with a mean particle diameter of less than 0.01 μm. With respect to the powder before the surface treatment in which the mean particle diameter exceeds 100 μm, cosmetics (compositions) obtained using the same give quite a rough feeling regarding the smooth feeling (touch) to impart an uncomfortable feeling to the skin, and in addition seem likely to decrease ready re-dispersibility or stability over an extended time period of the cosmetics (compositions). The particle diameter of such powder can be determined by measuring the particle diameter through observation by an optical microscope or an electron microscope and calculating the mean. As to particles in non-accurate sphere, the long size, short size and thickness are totally summed up to determine the mean size.

Any particle shape of the particles of the powder to be used before the surface treatment, which is used in the present invention, is satisfactory with no specific limitation but is selected from for example sphere shapes, bar shapes, needle shapes, plate shapes, indefinite shapes, scale shapes and biconvex (spindle-like). Preferably, the particle shape is sphere. As to the particle structure, additionally, any structure can be selected with no specific limitation and includes for example porous structures and non-porous structures.

As the hydrophilizing agent, a water-soluble polyoxyalkylene glycol derivative is used in accordance with the present invention. As the water-soluble polyoxyalkylene glycol derivative used in the present invention, there may be used water-soluble polyoxyalkylene glycol derivatives for pharmaceutical agents or cosmetics, including for example polyalkylene glycols, polyoxyalkylene alkyl ethers, and polyoxyalkylene esters.

The polyalkylene glycols include for example polyethylene glycol, polypropylene glycol, polyoxyethylene polyoxypropylene glycol, polyglycerin, polyoxyethylene glycerin, polyoxypropylene glyceryl ether, polyoxyethylene polyoxypropylene glyceryl ether, polyoxyethylene polyoxypropylene trimethylolpropane, polyoxyethylene diglyceryl ether, polyoxyethylene polyoxypropylene pentaerythritol ether, and polyoxypropylene sorbit. The polyoxyalkylene alkyl ethers include for example polyoxyethylene monoalkyl ether, polyoxyethylene cholesteryl ether, polyoxyethylene alkylphenyl ether, polyoxyethylene dinonylphenyl ether, polyoxypropylene alkyl ether, polyoxyethylene polyoxypropylene alkyl ether, polyoxyethylene methyl glucoside, and polyoxypropylene methyl glucoside. The polyoxyalkylene esters include for example polyoxyethylene monoester, polyoxypropylene glycol monoester, polyoxyethylene diester, polyoxyethylene alkyl ether ester, polyoxyethylene glyceryl fatty acid, and polyoxyethylene glyceryl isostearate. As them, commercially available ones from various manufacturers may be used. Among them, preferably, polyoxyethylene monoester, polypropylene glycol monoester, polyoxyethylene glyceryl fatty acid, and polyoxyethylene glyceryl isostearate may be used. More preferably, polyethylene glycol monooleate, and polypropylene glycol monooleate, polyoxyethylene glyceryl cocoate, polyoxyethylene glyceryl laurate, and polyoxyethylene glyceryl oleate may be used. Additionally, these may be used singly or in combination in mixture.

The amount of the water-soluble polyoxyalkylene glycol derivative to be contained is not specifically limited. As described below, the amount thereof is selected such that the total amount of the hydrophilizing agent is preferably approximately 0.01 to 50% by weight, more preferably approximately 0.2 to 40% by weight, still more preferably approximately 0.5 to 30% by weight of the powder before the surface treatment. Herein, the amount of the water-soluble polyoxyalkylene glycol derivative of itself is preferably approximately 0.01 to 20% by weight, more preferably approximately 0.1 to 15% by weight. When the amount thereof is less than 0.01% by weight, the hydrophilicity, the excellent dispersibility in aqueous dispersion medium, which are desired, and the good long-term dispersion stability cannot be gained. When the amount thereof exceeds 20% by weight, the effect corresponding to the amount cannot be obtained. Regarding the water-soluble polyoxyalkylene glycol derivative, those with various molecular weights are commercially available and may be used singly or in mixture.

In accordance with the present invention, the hydrophilizing agent preferably contains a water-soluble cationic polymer in addition to the water-soluble polyoxyalkylene glycol derivative. The water-soluble cationic polymer used in the present invention includes but is not limited to chitin derivatives such as chitosan, partially hydrolyzed chitin, chitosan-dl-pyrrolidonecarboxylate, succinylchitosan and hydroxypropylchitosan, dimethyldiallylammonium chloride derivatives such as a dimethyldiallylammonium chloride-acrylamide copolymer and polydimethylmethylenepiperidinium chloride, cationized celluloses such as o-[2-hydroxy-3-(trimethylammonio)propyl]hydroxyethylcellulose chloride and o-[2-hydroxy-3-(lauryldimethylammonio)propyl]hydroxycellulose chloride, quaternary nitrogen-modified polysaccharides such as cationized modified cellulose and cationized locust bean gum, cationized guar gums such as o-[2-hydroxy-3-(trimethylammonio)propyl] chloride guar gum, methacrylic acid derivatives such as a methacryloylethyldimethylbetaine-methacryloylethyltrimethylammonium chloride-methoxypolyethylene glycol methacrylate copolymer, a methacryloylethyldimethylbetaine-methacryloylethyltrimethylammonium chloride-2-hydroxyethyl methacrylate copolymer and a vinylpyrrolidone-N,N-dimethylaminoethyl methacrylate copolymer diethyl sulfate, vinylpyrrolidone derivatives such as a vinylpyrrolidone-dimethylaminoethyl methacrylate copolymer, a vinylpyrrolidone-methacrylamidopropyltrimethylammonium chloride copolymer and a vinylpyrrolidone-methylvinylimidazolium chloride copolymer, a dimethylallylammonium chloride-acrylamide copolymer containing diallyldimethylammonium chloride being a quaternary cationic monomer as a constituent, an acrylamide-acrylic acid-dimethyldiallylammonium chloride copolymer, polydimethylmethylenepiperidinium chloride, cathionized tamarind and the like. Preferably, at least one of dimethyldiallylammonium chloride-acrylamide copolymer, polydimethylmethylene piperidinium chloride, and o-[2-hydroxy-3-(trimethylammonio)propyl]hydroxyethylcellulose chloride is selected. Therefore, these may be used singly or in mixture.

The amount of the water-soluble cationic polymer to be contained is not specifically limited. As described below, the amount thereof when expressed as the total amount of the hydrophilizing agent is approximately 0.01 to 50% by weight, more preferably approximately 0.1 to 40% by weight, still more preferably approximately 0.5 to 30% by weight of the powder before the surface treatment. Herein, the amount of the water-soluble cationic polymer of itself is preferably approximately 0.001 to 20% by weight, more preferably approximately 0.01 to 15% by weight. When the amount thereof is less than 0.001% by weight, the hydrophilicity, the excellent dispersibility in aqueous dispersion medium, which are desired, and the good long-term dispersion stability cannot be gained. When the amount thereof exceeds 20% by weight, the effect corresponding to the amount cannot be obtained.

In accordance with the present invention, the hydrophilizing agent preferably contains a water-soluble cationic polymer and a low-molecular organosilicon derivative in addition to the water-soluble polyoxyalkylene glycol derivative. As the low-molecular organosilicon derivative used in the present invention, silanols having a polysiloxane molecule of an oligomer, containing some silicon-carbon (Si—C) bonds, silicon-hydroxy bonds (Si—OH) or Si—O—C bonds and having an alkylsilanol structure such as a methylsilanol or dimethylsilanol structure are selected which have high safety and high moisture retention and are quite excellent in activity of repairing and regenerating a tissue and affinity for the skin.

Generally, such low-molecular organosilicon derivative is represented by the following formula (I). However, low-molecular organosilicon derivatives to be hydrolyzed into those of the following formula (I) may also be satisfactory. These compounds are soluble in water and have biological activities.

[Chemical formula I]

$$X[R_nSi(OH)_{4-n}] \tag{1}$$

wherein $0<n<4$, $X>4$, and R represents an alkyl group.

The low-molecular organosilicon derivative includes for example monomethylsilanetriol mannuronate ($CH_3$—Si$(OH)_2$—O—$C_6H_9O_6$), dimethylsilanediol hyaluronate ($CH_3$—Si $(OR)_2$, in which R represents a hyaluronyl group), a mixture of silanol caffeate and silanol mannuronate, elastin peptide silane ($CH_3$—Si $(OH)_2OR$, in which R represents an elastin polypeptide), ascorbylmethylsilanol pectin, monomethylsilanetriol lactate ($CH_3$—Si $(OH)_2$—O—$C_3H_5O_2$), trioleyloxymonomethylsilane ($C_{56}H_{22}SiO_3$), methylsilanol triPEG-8-glyceryl cocoate ($CH_3$—Si $(OC_2H_4OR)_3$, in which R represents a coconut oil fatty acid glyceryl), lysine silanetriol, methylsilanol PCA copper, methylsilanol carboxymethyl theophylline alginate, dioleyl tocopheryl methylsilanol, methylsilanol alginate ester, silanetriol trehalose ether, silanetriol glutamate, asefuirin methylsilanol silanetriol hydrolyzed collagen mannuronate, *Asparagopsis armata* extract, dimethylsilanediol-butylene glycol-triethanolamine, dimethylsilanol-hyaluronic acid condensate, silanediol salicylate, methylsilanol-lactic acid condensate solution, aspartic acid-monohydroxyproline monomethylsilanol salt solution, methylsilanol-hydrolyzed elastin condensat, and dimethyloxobenzodioxasilane. Preferably, at least one of dimethylsilanediol hyaluronate, monomethylsilanetriol lactate, methylsilanol mannuronate and methylsilanol triPEG-5-glyceryl cocoate is selected. Thus, these may be used singly or in mixture.

The amount of the low-molecular organosilicon derivative to be contained is not specifically limited. As described below, the amount thereof when expressed as the total amount of the hydrophilizing agent is selected such that the total amount of the hydrophilizing agent is approximately 0.01 to 50% by weight, more preferably approximately 0.2 to 40% by weight, still more preferably approximately 0.5 to 30% by weight of the powder before the surface treatment. Herein, the amount of the low-molecular organosilicon derivative of itself is preferably approximately 0 to 10% by weight, more preferably approximately 0 to 5% by weight. When the amount thereof exceeds 10% by weight, any effect corresponding to the amount cannot be obtained.

By allowing the hydrophilizing agent used in the present invention (the water-soluble polyoxyalkylene glycol derivative, the water-soluble cationic polymer and the low-molecular organosilicon derivative) to be adsorbed or coated on the surface of the powder comprising the silicone resin and/or the organic powder, the water absorption property (water absorption amount) or oil absorption property (oil absorption amount) inherent in the powder to be surface-treated can be modified, so that effects of inhibiting a rough feeling of the skin which could not be removed with ordinary powders and causing the makeup to come off through improvement of adhesion to the skin, and also to attain novel organoleptic properties (sensory characteristics) (elasticity and tonicity of the skin in the long-term and continuous use, and the like), stable, ready re-dispersibility over an extended time period (with long-term lapse of time) in an aqueous system and stability over an extended time period for cosmetics (cosmetic compositions) are achieved. The coated film of the surface-treating substance is firmly adhered on the surface of particles of the powder described above in acidic and alkaline conditions, specifically with pH between 3 and 13 without being dissolved.

The amount of the hydrophilizing agent can be selected, depending on the particle shape of each powder to be surface-treated and the mean particle diameter thereof, with no specific limitation. The total amount of the hydrophilizing agent may preferably be selected from approximately 0.01 to 50% by weight, more preferably approximately 0.2 to 40% by weight, still more preferably approximately 0.5 to 30% by weight of the powder before the surface treatment.

In accordance with the present invention, the surface treatment (coating) of the powder before the surface treatment for use in accordance with the present invention can be done by using singly the water-soluble polyoxyalkylene glycol derivative or by using the water-soluble polyoxyalkylene glycol derivative with (in combination with) the water-soluble cationic polymer or with (in combination with) the water-soluble cationic polymer and the low-molecular organosilicon derivative. For the surface treatment with a combination of the water-soluble polyoxyalkylene glycol derivative and the water-soluble cationic polymer, the surface may be treated simultaneously with the water-soluble polyoxyalkylene glycol derivative and the water-soluble cationic polymer. Otherwise, the surface may be treated first with any one of the water-soluble polyoxyalkylene glycol derivative and the water-soluble cationic polymer and then with the remaining hydrophilizing agent. For the surface treatment with a combination of the water-soluble polyoxyalkylene glycol derivative, the water-soluble cationic polymer and the low-molecular organosilicon derivative, additionally, the water-soluble polyoxyalkylene glycol derivative, the water-soluble cationic polymer and the low-molecular organosilicon derivative are mixed together for simultaneous surface treatment; otherwise, any one or more of the water-soluble polyoxyalkylene glycol derivative, the water-soluble cationic polymer and the low-molecular organosilicon derivative is first used for the surface treatment, and then, any one or more of the remaining hydrophilizing agents is used for the surface treatment, followed by the surface treatment with the last one.

For the surface treatment (hydrophilic treatment) with the hydrophilizing agent, the particle surface of the powder before the surface treatment is directly treated with the hydrophilizing agent, for hydrophilization treatment. The treatment can be done by adding for example the water-soluble polyoxyalkylene glycol derivative, the water-soluble cationic polymer, the low-molecular organosilicon derivative and the powder particle before the surface treatment to an aqueous dispersion medium, specifically water and/or water-soluble solvents, for mixing them together. The surface-treated powder can be obtained by drying the resulting mixture. If necessary, then, the mixture is washed with water and filtrated, in a repeated manner, to remove contaminants. The resulting product is subjected to processes such as drying and pulverization. For these treatment processes themselves, any known method(s) may be employed.

In the surface-treatment method, the amount of the mixture solution of the powder before the surface treatment, water and/or a water-soluble solvent and a hydrophilizing agent is adjusted, for dry mixing or kneading methods at the pendular state, for kneading methods at the pendular to capillary states, and for slurry methods at the slurry state.

The states of the mixture of the powder with liquids are described in references, such as the Dictionary of Powder Engineering (Terminology Dictionary of Powder Technology (Funtai Kogaku Yogo Jiten) (Nikkan Kogyo Shinbunsha, issued in Showa 56 (1981)). The states are summarized in Table 1. When water is added to a group of particles in an approximately sphere shape and an approximately equal size as filled in the most dense state, water adheres in a circular form with the center in contact with the particles when water is first in a small amount, so that water exists discontinuously (the pendular state); when the amount of water increases, the water circle increases of the size, so that the circles are finally connected together, leading to the formation of a continuous structure of water (the liquid phase), the particles (the solid phase) and air (the gaseous phase) (the funicular I state); when the amount of water further increases, the liquid phase closes on a face including the contact points with the particles, so that the air phase turns inconsistent (the funicular II state); when the amount of water increases more, air in independent foams decreases of its volume, so that the volume is decreased to 0, to cause the continuous structure of only the two phases of the solids and the liquid (the capillary state). Then, the water content at the transfer of the funicular II state to the capillary state is called plastic limit, while the water content at the transfer of the capillary state to the slurry state is called liquid limit. It is confirmed with a loupe and the like as to in which region the form (state) of the mixture is.

TABLE 1

| | Mixture State | | | | |
|---|---|---|---|---|---|
| | Pendular region | Funicular I region | Funicular II region | Capillary region | Slurry region |
| Solid | continuous | continuous | continuous | discontinuous | discontinuous |
| Liquid | discontinuous | continuous | continuous | continuous | continuous |
| Gas | continuous | continuous | discontinuous | none | none |

For the surface treatment (coating) of a pigment powder with the low-molecular organosilicon derivative or with the low-molecular organosilicon derivative and the water-soluble cationic polymer, slurry methods were used to produce the coated powder, as described in the application filed by the present inventors (refer to Japanese Patent Application No. 2004-021659 and the Japanese Patent Application No. 2004-057674). However, a stronger mechano-chemical action is further exerted when the powder is mixed between pendular state and capillary state, so that a stronger bond between the powder and the treating agent can be generated. For the production (surface treatment) of the surface-treated powder of the present invention, therefore, the amount of the mixture solution of the powder before the surface treatment, water and/or a water-soluble solvent and a hydrophilizing agent is preferably adjusted between pendular state and capillary state, for a dry mixing process or a kneading process for the surface treatment. For more uniform treatment, a kneading process is more preferable.

As the apparatus for dry mixing or kneading which can be used in the present invention, kneading apparatuses which have been known or will be developed in future can be selected. For example, among kneading apparatuses of wheel type, blade type, and roll type and other types of kneading apparatuses, at least one may be selected. The kneading apparatus of the wheel type includes for example Simpson mix muller, Eirich mill, multi-mill, Stotz mill, wet pan, and melanger. The blade type kneading apparatus includes for example kneader, pressure kneader, helical rotor, screw extruder, extruder, KRC kneader, ultimate kneader, puddle mixer, ribbon mixer, mix master, pony mixer, high sludger, vortex mixer, Nauta mixer, all-purpose mixer, thermal mixer, Henschel mixer, cutter mixer, speed mixer, Daino mixer, mechano-fusion, Nobiruta, and Nanocula. The roll type kneading apparatus includes for example roll mixer, three-roll, taper roll, Banbury mixer, and gear compounder. Other types of such apparatuses include for example automated mortar, JET atomizer, fluid layer, and spray dryer.

The water-soluble solvent(s) is selected from water-dissolvable solvent(s) of any composition. Example of the solvent includes lower alcohols of one to 5 carbon atoms, such as ethanol and isopropanol; glycols with 2 to 8 carbon atoms, such as ethylene glycol, propylene glycol, 1,3-butylene glycol and dipropylene glycol; $C_3$ and $C_4$ ketones and $C_2$ to $C_4$ aldehydes. These may be used singly or in mixture of two or more thereof. Among them, lower alcohols such as methanol, ethanol, propanol and isopropanol are preferable because these alcohols can form stronger hydrophilized coating films.

The alcohols may be added simultaneously with the hydrophilizing agent. Additionally, the alcohols are first added, followed by addition of the hydrophilizing agent for the surface treatment. Alternatively, the hydrophilizing agent is first added, followed by the addition of the alcohols for the surface treatment.

In case that the powder before the surface treatment is coated with the hydrophilizing agent by kneading in producing the surface-coated powder in accordance with the present invention, preferably, the coating is done under the addition of an appropriate alkali, so as to form a stronger hydrophilized coating film. The alkali includes for example but is not limited to at least one selected from alkali metal hydroxides, alkali earth metal hydroxides, primary-, secondary- and tertiary alkylamines, or primary-, secondary- or tertiary alkanolamines and alkaline buffers, such as sodium hydroxide, potassium hydroxide, calcium hydroxide, magnesium hydroxide, ammonia, aqueous ammonia, triethanolamine, dimethylamine, diethylamine, trimethylamine, triethylamine, triisopropanolamine, trisodium phosphate, disodium hydrogen phosphate, dipotassium hydrogen phosphate, monoethanolamine, diethanolamine, diisopropanolamine, and polyethanolamine. These may be used singly or in mixture.

The amount of the alkali to be added is not specifically limited, which is preferably selected as approximately 0.01 to 10% by weight. When the alkali amount to be added is less than 0.01% by weight, the effect due to the addition cannot be obtained. When the amount of alkali to be added exceeds 10% by weight, the alkali remains on the surface-treated powder, so that a process of rinsing off the remaining alkali is required. Depending on the powder, the powder may potentially be modified with the alkali.

The alkali may be added, simultaneously with the hydrophilizing agent, before the surface-treating agent is added, or after the surface-treating agent is added.

In case that the powder before the surface treatment is coated with the hydrophilizing agent by kneading in producing the surface-treated powder in accordance with the present invention, a heating process is preferably done during kneading and/or after kneading, to form a stronger hydrophilized coating film. The temperature for the heating process includes but is not limited to a range of approximately 50 to 160° C., preferably a range of approximately 60 to 150° C., more preferably a range of approximately 70 to 130° C. When the temperature for the heating process is less than 50° C., the effect of the heating process cannot be obtained. When the temperature for the heating exceeds 160° C., alternatively, the hydrophilizing agent cannot exist, stably, causing for example the decomposition of the hydrophilizing agent. Although the coated film after the heating process gets hard, the desired hydrophilicity and dispersibility cannot be obtained. Herein, the heating process is preferably done after kneading, because the handleability in for example drawing out the powder is readier.

For the production of the surface-treated powder in accordance with the present invention, the alkali and the alcohol may be added separately or simultaneously. In that case, the hydrophilizing agent may be added simultaneously or the hydrophilizing agent is used for the surface treatment after the alkali and/or the alcohol is first added. Alternatively, the alkali and/or the alcohol may be added for the surface treatment, after the hydrophilizing agent is added.

The heating process is satisfactorily done at a state with addition of the alkali and/or the alcohol; at the heated state, the alkali and/or the alcohol may be added. In that case, the hydrophilizing agent may be added simultaneously or the hydrophilizing agent is used for the surface treatment after the alkali and/or the alcohol is first added. Alternatively, the alkali and/or the alcohol may be added for the surface treatment, after the hydrophilizing agent is added.

In the production of the surface-treated powder in accordance with the present invention, the hydrophilizing agent causes a gelation during the coating of the powder to be surface-treated with the hydrophilizing agent, so that the coated film is formed on the surface of the powder to be surface-treated. Then, the hydrophilizing agent which has not participated in the gelation may sometimes remain. Additionally, the alkali and/or the alcohol added as an additive may sometimes remain on the powder surface. In that case, these unreactive substances may satisfactorily be removed, for example by washing with water, after the surface treatment.

(Dispersion of the Invention)

The dispersion of the present invention contains the surface-treated powder of the present invention. The surface-treated powder is uniformly dispersed in the aqueous dispersion medium such as water, specifically even in acidic and alkaline conditions (specifically with pH from 3 to 13), stably over the course of time. Thus, the dispersion of the present invention has very excellent dispersibility, storage stability, and applicability, especially as a dispersion for cosmetics. Hence, a great improvement can be made of powder functions greatly variable depending on the dispersion state of the powder particle, for example affixture to the skin (adhesion), touch (smooth feeling), gloss and transparency.

In the dispersion of the present invention, one or two or more types of the surface-treated powder may be contained in aqueous dispersion medium. Such dispersions may also be encompassed within the scope of the present invention.

Preferably, the dispersion of the present invention has a composition as simple as possible. The content of the surface-treated powder is not specifically limited. The surface-treated powder may be contained at an appropriate ratio. Herein, the surface-treated powder may be at a content of preferably 0.1 to 95% by weight, particularly preferably 0.1 to 90% by weight. In case of incorporating such dispersion in a cosmetic, the surface-treated powder described above is directly mixed with an aqueous dispersion medium or a non-aqueous dispersion medium and other components if necessary, to prepare a cosmetic. Otherwise, the surface-treated powder is firstly mixed with an aqueous dispersion medium or a non-aqueous dispersion medium, to prepare the dispersion of the present invention, and using the resulting dispersion, then, a cosmetic may be prepared.

For various purposes so as to more highly disperse the surface-treated powder, to more stabilize the dispersion, or to improve the functions of the dispersion in a synergistic effect with a third component, or the like, the third component or other components may be contained in the dispersion of the invention. Components to be contained for such purposes include various surfactants, for example anionic surfactants including alkyl ether sulfate ester salts such as POE lauryl sulfate triethanolamine; alkylbenzene sulfonate salts such as sodium dodecylbenzene sulfonate; higher alkyl sulfate ester salts such as potassium lauryl sulfate and potassium lauryl sulfate; higher fatty acid amide sulfonate salts such as N-acyl-sarcosinic acid and sodium N-myristoyl-N-methyltaurine; higher fatty acid ester sulfate ester salts such as hardened glycerin cocoate sodium sulfate; higher fatty acid ester sulfonate salts, higher fatty acid alkylolamide sulfate ester salts, fatty acid soap, sulfosuccinate salts, secondary alcohol sulfate ester salts, POE alkyl ether carboxylate, POE alkylallyl ether carboxylate salts, α-olefin sulfonate salts, lauroyl monoethanolamide sodium succinate, N-palmitoylaspartate diethanolamine and sodium casein; cationic surfactants including alkyltrimethylammonium salts such as stearyltrimethylammonium chloride, alkylpyridinium salts such as distearyldimethylammonium dialkyldimethylammonium salts, alkyl quaternary ammonium salts, alkylamine salts, alkyldimethylbenzylammonium salts, alkylisoquinolinium salts, dialkylmorphonium salts, POE alkylamine, polyamine fatty acid derivatives, amyl alcohol fatty acid derivatives, benzalkonium chloride, and benzethonium chloride; nonionic detergents including imidazoline-based amphoteric surfactants such as 2-cocoyl-2-imidazolinium hydroxide-1-carboxyethyloxy disodium salt, betaine-based amphoteric surfactants such as alkyl betaine, amide betaine, and lauryldimethylaminoacetate betaine, glycerin fatty acid esters such as glycerin sesquioleate and glycerin monostearate, polyglycerin fatty acid esters such as hexaglyceryl polyricinoleate, diglyceryl monostearate and decaglyceryl decaoleate, sorbitan fatty acid esters such as sorbitan monooleate and sorbitan sesquioleate, propylene glycol fatty acid esters such as propylene glycol monostearate, POE sorbitan fatty acid esters such as POE sorbitan monooleate, POE glycerin fatty acid esters such as POE glycerin triisostearate, POE fatty acid esters such as POE monooleate and POE distearate, POE alkyl ethers such as POE lauryl ether and POE stearyl ether, POE-POP alkyl ethers such as POE-POP hydrogenated lanoline, hardened castor oil derivatives, glycerin alkyl ether, alkanolamide, sucrose fatty acid ester, dextrin fatty acid ester, inulin fatty acid esters, and hydroxystearic acid; and additionally, phospholipids such as lecithin; sugar lipids such as trehalose lipid; and fluorine-based surfactants such as perfluoroalkylphosphate salts, perfluoroalkylsulfonate salts, and perfluoroalkylcarboxylate salts.

Furthermore, the dispersion of the present invention is contained partially with any water-soluble substance which has been so far employed, unless the effects of the present invention are impaired, to prepare a dispersion.

The water-soluble substance includes for example alcohols such as methanol, ethanol, and propyl alcohol; sodium chloride, magnesium chloride, magnesium sulfate, potassium chloride, magnesium bromide and hydrated salts thereof and mixtures thereof; inorganic salts such as bittern; amino acids such as alanine, glycine, and pyrrolidone carboxylic acid and salts thereof; solubilized peptides such as hydrolyzed collagen, hydrolyzed elastin, hydrolyzed fibroin, and hydrolyzed sericin; 2-hydroxy acids such as lactic acid and citric acid, and salts thereof and derivatives thereof; urea; divalent alcohols such as propylene glycol, dipropylene glycol, 1,3- butylene glycol, and 1,2-pentanediol; glycerin and polyglycerins such as diglycerin and triglycerin; sugars such as glucose and sucrose; sugar alcohols such as sorbitol and maltitol; mucopolysaccharides such as hyaluronic acid, and chondroitin sulfate; water-soluble polymers such as carboxyvinyl polymer, hydroxyethylcellulose, and xanthan gum; water-soluble ultraviolet absorbents such as p-aminobenzoic acid, p-methoxycinnamic acid, sodium 2-hydroxy-4-methoxybenzophenone-5-sulfonate, and sodium dihydroxydimethoxybenzophenonesulfonate; water-soluble vitamins such as thiamine and derivatives thereof (vitamin $B_1$), riboflavin (vitamin $B_2$), pyridoxine and derivatives thereof (vitamin $B_6$), ascorbic acid and derivatives thereof (vitamin C), and pantothenic acid and derivatives thereof; water-soluble anti-inflammation agents such as dipotassium glycyrrhizate and sodium guaiazulene sulfonate; water-soluble astringents such as tannic acid; animal extracts such as placenta extract and spleen extract; various vegetable extracts, yeast extracts, and algae extracts.

As the method for dispersing the surface-treated powder used in the present invention in a dispersion medium, known methods may be used with no specific limitation. An oily dispersion can be produced, using for example mixers such as kneader, Henschel, roll, and extruder, and wet mixing- and dispersing machines such as propeller mixer, high speed mixer, dissolver, disper, homogenizer, altemizer, wet jet mill, colloidmill, mass colloider, beadmill, sandmill, basketmill and ultra-high pressure homogenizer.

In the present invention, the surface-treated powder of the present invention as described above may be dispersed in a non-aqueous dispersion medium, using a given method, to prepare a non-aqueous type dispersion. When washing such as water-washing or filtration and washing is never done or is done at a low level in producing the surface-treated powder of the present invention, for example, the excess hydrophilizing agent (which has not participated in the gelation) remaining on the surface of the surface-treated powder functions as a dispersing agent (surfactant). Hence, the surface-treated powder of the present invention may potentially be dispersed uniformly in a non-aqueous dispersion medium. Additionally, the surface-treated powder of the present invention can be dispersed uniformly in a non-aqueous dispersion medium, using the surfactant. As the non-aqueous dispersion medium, non-aqueous medium (media) in liquid at ambient temperature is used. Specifically, such non-aqueous dispersion medium includes for example hydrocarbons such as fluid paraffin and squalene; polyhydric alcohol fatty acid esters such as tri(caprylic-capric) glyceril, and glyceryl tri2-ethylhexanoate; fatty acids such as isostearic acid, oleic acid, linoleic acid and linolenic acid; higher alcohols such as isostearyl alcohol, myristyl alcohol and lauryl alcohol; silicone oils such as cyclic or linear dimethylpolysiloxane, and methylphenylpolysiloxane; ester oils such as cetyl 2-ethylhexanoate, octyl palmitate, cetyl isooctanoate, 2-octyldodecyl pivalate, 2-hexyldecyl 16-methylheptadecanoate, 2-octyldodecyl tetradecanoate, ethyl cis-12-octadecadienoate, phytosteryl 16-methylheptadecanoate, and isopropyl cis-12-octadecadienoate; and vegetable oils such as avocado oil, olive oil, sunflower oil, hazel nut oil, rose hip oil, *Aleurites moluccana* seed oil, jojova oil, macademia nut oil, coconut oil and apricot kernel oil. One or two or more types of the non-aqueous dispersion medium may be used in appropriate combination. In case that the non-aqueous dispersion containing the surface-treated powder of the present invention (the dispersion prepared by dispersing the surface-treated powder of the present invention in the non-aqueous dispersion medium) is mixed and agitated with an aqueous dispersion medium, the surface-treated powder of the present invention contained in the non-aqueous dispersion transfers to the aqueous dispersion medium.

(Cosmetic of the Invention)

The cosmetic of the present invention is a cosmetic containing the surface-treated powder or the dispersion described above. The surface-treated powder can be prepared as described above, and also the dispersion can be prepared as described above.

The agent form of the cosmetics of the present invention is not particularly limited. As the agent form of the cosmetic, there is selected any one of for example aqueous products, emulsified products, oily products, powdery products, aerosol products, solid products and tablet products. Additionally, these may be alkaline agent forms. Specifically, the agent form includes for example rinsing cosmetic products such as soap, body shampoo, rinsing powder, facial rinsing cream, and cleansing cream; basic cosmetic products such as lotion, after-shaving lotion, cologne, pre-shaving lotion, hand lotion, suntan lotion, sunscreen lotion, carmine lotion, acne lotion, deodorant lotion, shake lotion, after-shaving cream, cold cream, shaving cream, body gel, massage gel, emulsion, beauty liquid, vanishing cream, hand cream, suntan cream, sunscreen cream, and packs; finish cosmetic products such as foundation, powder foundation, pressed powder, cream foundation, liquid foundation, solid foundation, creamy face powder, solid face powder, face powder, talcum powder, face powder in paste, baby powder, body powder, watery face powder, lipstick, rouge, lip cream, lip liner, eye cream, eye shadow, eye liner, mascara, eyebrow pencil, nail enamel, nail color, nail polish, and nail cream; cosmetic products for scalp and hair, such as hair washing powder, shampoo, dry shampoo, hair oil, hair combing oil, hair cream, hair rinse, conditioner, hair growth agent, hair restorer, hair remover, hair dye, hair bleach, hair mascara, hair color, hair tonic, setting agent, chick, hair oil, hair spray, hair liquid, hair moose, hair styling gel, permanent-wave agent, pomade, hairdressing, and hair styling gel; deodorant cosmetic products such as deodorant cream, deodorant soap, ointment, and aerosol; dental pastes such as powdery dental paste, dental paste and aqueous dental paste; bath agents such as bath oil and bath salt; and aromatic products such as aromatic soap, toilet deodorant, aromatic oil, cologne, and perfume. As the agent form of the cosmetic of the present invention, specifically, hair mascara, jelly pack, gel foundation, carmine lotion, pre-shave lotion, powder foundation, lipstick, shampoo, soap, oil-in-water type (O/W) liquid foundation, aqueous nail enamel or emulsion is selected in particular.

The surface-treated powder of the invention is at a state with hydrophilicity, without any deterioration of the characteristic features of silicone resins or organic powders, for example smoothness, touch, extension (spreadability) on skin, and transparent feeling and impact resistance. Therefore, a cosmetic excellent in ready re-dispersibility, long-term dispersion stability with lapse of time, moist touch, adhesion to the skin in applying thereon, extension (spreadability) on skin, and transparent feeling, and having high impact resistance can be obtained. Specifically, when a jelly pack is selected as the agent form, the cosmetic has a great effect of extension (spreadability) on skin. When a gel foundation is selected, it is excellent in adhesion to skin and also effect of longer wear. When a carmine lotion is selected, an effect of extension (spreadability) on skin is good, a moist touch is imparted to the skin, and a refreshed (cool) feeling is also provided. When the emulsion is selected, affinity for skin (absorption feeling to the skin) is good, effects of tonicity and elasticity of skin are excellent, drab is improved, and a transparent feeling of skin is excellent.

In the present invention, the preparation (production) of the cosmetics is not particularly difficult, and the desired cosmetics can be obtained by any technique (for example, emulsification) which has been so far employed in using a surface-treated powder or dispersion for cosmetics.

When the surface-treated powder of the present invention is contained in cosmetics (cosmetic compositions), the amount (mixed amount) thereof is not particularly limited. It is preferably from 0.1 to 99% by weight or so, more preferably from 0.1 to 95% by weight or so based on the total cosmetic composition. Further, when the dispersion of the present invention is contained in the cosmetics, its amount is not particularly limited.

The cosmetics of the present invention can further contain, as required, other components routinely used for cosmetics unless the objects and effects (dispersibility, long-term dispersion stability and the like) of the present invention are impaired. Examples thereof include ultraviolet absorbents (ultraviolet light absorbing agent (absorber)), liquid fats and oils, solid fats and oils, liquid or solid fats and oils, waxes, ester oils, hydrocarbon oils, silicones, lower alcohols, sterols, humectants, sequestering agents, neutralizers, pH adjusting agents, antioxidants, antibacterial agents, various extracts, medicaments, and the like.

The ultraviolet absorbents include for example cinnamic acid-based (type) ultraviolet absorbents such as octylcinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate, 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, ethylhexylmethoxycinnamate, and glyceryl mono-2-ethylhexanoyl-diparamethoxycinnamate; benzophenone-based ultraviolet absorbents such as 2,4-dihydroxybenzophenone, 2,2'-dihydroxy-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate salt, sodium phenylbenzimidazole sulfonate, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; para-aminobenzoic acid-based ultraviolet absorbents such as PABA monoglycerin ester, ethylhexyldimethyl PABA, N,N-dipropoxy PABA ethyl ester, N,N-diethoxy PABA ethyl ester, N,N-dimethyl PABA ethyl ester, N,N-dimethyl PABA butyl ester, and N,N-diethyl PABA methyl ester; salicylic acid-based ultraviolet absorbents such as aminosalicylate, ethylhexyl salicylate, menthyl salicylate, homomethyl salicylate, octyl salicylate, phenyl salicylate, benzyl salicylate, and p-isopropanol phenyl salicylate; anthranylic acid-based ultraviolet absorbents such as methyl anthranilate; and ultraviolet absorbents such as 3-(4'-methylbenzylidene)-d-camphor, 3-benzylidene-d, 1-camphor, urokanic acid, urokanic acid ethyl ester, octyltriazone, 2-phenyl-5-methylbenzoxazol, 2-(2'-hydroxy-5'methylphenyl) benzotriazol, bicetylhexyloxyphenol methoxyphenyltriazine, 4-methoxy-4'-t-butyldibenzoylmethane, octocrylene, methylene bisbenzotriazolyl tetramethylbutylphenol and homosalate. The amount (mixed amount) of these ultraviolet absorbents is not particularly limited, and a high ultraviolet light preventive (protective) effect is obtained with a small amount thereof.

The liquid fats and oils include for example linseed oil, *Aleurites moluccana* seed oil, camellia oil, macadamia nut oil, corn oil, mink oil, olive oil, avocado oil, sasanqua oil, castor oil, safflower oil, apricot kernel oil, cinnamon oil, jojoba oil, grape oil, sunflower oil, almond oil, rapeseed oil, sesame oil, wheat germ oil, rice germ oil, rice bran oil, cottonseed oil, soybean oil, peanut oil, tea seed oil, evening primrose oil, egg yolk oil, neatsfoot oil, liver oil, triglycerin, glycerin trioctanoate, glycerin triisopalmitate and the like.

The solid fats and oils include for example cacao butter, beef tallow, mutton tallow, lard, horse fat, hardened oil, hardened castor oil, Japan wax, shea butter and the like.

The liquid or solid fats and oils include for example coconut oil, palm oil, palm kernel oil and the like.

The waxes include for example beeswax, candelilla wax, cotton wax, carnauba wax, bayberry wax, Chinese wax, spermaceti wax, montan wax, bran wax, lanoline, reduced lanoline, hard lanoline, kapok wax, sugar cane wax, jojoba wax, shellac wax and the like.

The ester oils include for example octanoates (octanoic acid esters) such as cetyl octanoate, isooctanoates (isooctanoic acid esters) such as glycerin tri-2-ethylhexanoate and pentaerythritol tetra-2-ethylhexanoate, laurates (lauric acid esters) such as hexyl laurate, myristates (miristic acid esters) such as isopropyl myristate and octyldodecyl myristate, palmitates (palmitic acid esters) such as octyl palmitate, stearates (stearic acid esters) such as isocetyl stearate, isostearates (isostearic acid esters) such as isopropyl isostearate, isopalmitates (isopalmitic acid esters) such as octyl isopalmitate, oleates (oleic acid esters) such as octyldodecyl oleate, adipic acid diesters such as diisopropyl adipate, sebacic acid diesters such as diethyl sebacate, diisostearyl maleate and the like.

The hydrocarbon oils include for example liquid paraffin, ozocerite (ozokerite), squalane, squalene, pristane, paraffin, isoparaffin, ceresin, vaseline (petrolatum), microcrystalline wax and the like.

The silicone includes for example linear silicones such as dimethylpolysiloxane, methylphenylpolysiloxane and methylhydrogenpolysiloxane, and cyclic silicones such as octamethylcyclotetrasiloxane, decamethylcyclopentasiloxane and dodecamethylcyclohexasiloxane.

The lower alcohols include for example methanol, ethanol, propanol, isopropanol and the like.

The sterol includes for example cholesterol, sitosterol, phytosterol, lanosterol and the like.

The humectants include for example 1,2-pentanediol, 1,2-hexanediol, 1,2-heptanediol, polyethylene glycol, propylene glycol, dipropylene glycol, 1,3-butylene glycol, hexylene glycol, glycerin, diglycerin, sorbitol and the like.

The sequestering agents include for example alanine, sodium edetate in the form of salt, sodium polyphosphate, sodium metaphosphate, phosphoric acid and the like.

The neutralizers agents include for example 2-amino-2-methyl-1-propanol, 2-amino-2-methyl-1,3-propanediol, potassium hydroxide, sodium hydroxide, amino acids such as L-arginine and L-lysine, triethanolamine, sodium carbonate and the like.

The pH adjusting agents include for example lactic acid, citric acid, glycolic acid, succinic acid, tartaric acid, dl-malic acid, potassium carbonate, sodium hydrogencarbonate, ammonium hydrogencarbonate and the like.

The antioxidants include for example ascorbic acid, α-tocopherol, dibutylhydroxytoluene, butylhydroxyanisol and the like.

The antibacterial agents include for example benzoic acid, salicylic acid, carbolic acid, sorbic acid, para-oxybenzoate, para-chloromethacresol, hexachlorophene, benzalkonium chloride, chlorhexidine chloride, trichlorocarbamide (trichlorocalbanilide?), sensitizing dyes, phenoxyethanol and the like.

The various extracts include for example saururaceae extract, phellodendron bark extract, melilot extract, dead nettle extract, glycyrrhiza extract, peony root extract, soapwort extract, gourd extract, cinchona extract, strawberry geranium extract, sophora extract, nuphar extract, fennel extract, primrose extract, rose extract, Rehmannia root extract, lemon extract, lithospernum root extract, aloe extract, calamus extract, eucalyptus extract, field horsetail extract, sage extract, thyme extract, tea extract, seaweed extract, cucumber extract, clove extract, brawble extract, melissa extract, ginseng extract, carrot extract, horse chestnut extract, peach extract, peach leaf extract, mulberry extract, crop weed extract, hamamerris liquid extract, placenta extract, thymus grand extract, silk liquid extract and the like.

The medicaments include for example vitamins such as vitamin A oil, retinol, retinol palmitate, inositol, pyridoxine hydrochloride, benzyl nicotinate, nicotinic acid amide, DL-α-tocopherol nicotinate, ascorbic acid magnesium phosphate, vitamin D2 (ergocalciferol), dl-α-tocopherol, dl-tocopherol, 2-L-ascorbic acid diester potassium, acetic acid dl-α-tocopherol, pantothenic acid and biotin; hormones such as estradiol and ethinyl estradiol; amino acids such as arginine, aspartic acid, cystine, cysteine, methionine, serine, leucine and tryptophan; anti-inflammatory agents such as allantoin, glycyrrhethinic acid and azulene; whitening agents such as arbutin; astringents such as zinc oxide and tannic acid; refrigerants such as L-menthol and camphor; sulfur; lysozyme chloride; pyridoxine chloride; and γ-oryzanol. Besides, the above medicaments can be used in a free state, those capable of salt formation can be used not only in a free state but also in the form of a salt of an acid or a base if the medicament is of the salt-making type. On the other hand, the medicaments having a carboxylic acid group can be used in the form of an ester.

The cosmetics of the present invention can contain, as required, any suitable perfumes, colorants, and the like unless the objects and the effects (dispersibility, long-term dispersion stability and the like) of the present invention are impaired.

(Use Other than Cosmetics)

The foregoing surface-treated powder (the surface-treated powder of the present invention) and the foregoing dispersion (the dispersion of the present invention) can be used not only for cosmetics but also for dispersions (dispersion compositions) widely used in various fields of additives of plastic products such as plastic films and plastic sponges, dispersion aids for inks, sequestering paints, toners (magnetic powders), synthetic resins, rubbers, silicones, chemical fibers, materials for packing, electronic materials, liquid crystal-associated materials, pigments and ceramics, solidification inhibitors and optical diffusing agents blocking inhibitors, or slipping inhibitor of information recording paper, and the like. Especially when the powder, which can be used in cosmetics is used in other fields and the dispersion is likewise required, the above surface-treated powder and the dispersion, which are used for cosmetics can also be employed in the other fields.

EXAMPLES

The present invention is illustrated more specifically below by referring to Examples. However, the present invention is not limited thereto.

Production Example 1

Production (Preparation) of Hydrophilicaly Treated Nylon 50 g of nylon (the trade name: Nylon SP-500 manufactured by Toray Co., Ltd.) was placed in a 25-liter Henschel mixer. Under agitation with the Henschel mixer, 100 g of PEG-12 glyceryl laurate was gradually charged, for 10-min agitation while the resulting mixture remained as it was. The resulting powder was taken out, dried and pulverized, to obtain the desired nylon with the surface hydrophilicaly treated.

Production Example 2

Production of Hydrophilicaly Treated Polystyrene 50 g of polystyrene (the trade name: GS-0605, manufactured by Ganz Chemical Co., Ltd.) was placed in a 100-cc kneader. Under agitation with the kneader, a mixture of 5 g of PEG-12 glyceryl laurate and 10 g of water was gradually charged for 10-min agitation while the resulting mixture remained as it was. Additionally, to the mixture thus obtained, 5 g of o-[2-hydroxy-3-(trimethylammonio)propyl] chloride guar gum was gradually added, for 10-min agitation. The resulting powder was taken out, washed with water, and filtered and cleansed. Subsequently, the resulting mixture was dried and pulverized, to obtain the desired polystyrene with the surface hydrophilicaly treated.

Production Example 3

Production of Hydrophilicaly Treated PMMA 2000 g of PMMA (the trade name: GMX-0615, manufactured by Ganz Chemical Co., Ltd.) was placed in a 25-liter Henschel mixer. Under agitation with the Henschel mixer, a mixture of 100 g of polypropylene glycol-26 oleate and 2 g of monomethylsilanetriol lactate was gradually charged for 10-min agitation while the resulting mixture remained as it was. Additionally, to the mixture thus obtained, 50 g of a dimethyldiallylammonium chloride-acrylamide copolymer was gradually added, for 20-min agitation. The resulting powder was taken out, washed with water, and filtered and cleansed. Subsequently, the resulting mixture was dried and pulverized, to obtain the desired PMMA with the surface hydrophilicaly treated.

Production Example 4

Production of Hydrophilicaly Treated Polystyrene 2000 g of polystyrene (the trade name: GS-0605, manufactured by Ganz Chemical Co., Ltd.) was placed in a 25-liter Henschel mixer. Under agitation with the Henschel mixer, a mixture of 200 g of PEG-12 glyceryl laurate and 100 g of 0.001 M KOH was gradually charged for 10-min agitation while the resulting mixture remained as it was. Additionally, to the mixture thus obtained, 200 g of o-[2-hydroxy-3-(trimethylammonio)propyl] chloride guar gum was gradually added, for 20-min agitation. The resulting powder was taken out, washed with water, and filtered and cleansed. Subsequently, the resulting mixture was dried and pulverized, to obtain the desired polystyrene with the surface hydrophilicaly treated.

Production Example 5

Production of Hydrophilicaly Treated Nylon 2000 g of nylon (the trade name: Nylon SP-500 manufactured by Toray Co., Ltd.) was placed in a 25-liter Henschel mixer. Under agitation with the Henschel mixer, a mixture of 100 g of polypropylene glycol-26 oleate and 10 g of ethanol was gradually charged for 10-min agitation while the resulting mixture remained as it was. Additionally, to the mixture thus obtained, 20 g of o-[2-hydroxy-3-(trimethylammonio) propyl] chloride guar gum was gradually added, for 20-min agitation. The resulting powder was taken out, washed with water, and filtered and cleansed. Subsequently, the resulting mixture was dried and pulverized, to obtain the desired nylon with the surface hydrophilicaly treated.

Production Example 6

Production of Hydrophilicaly Treated Silicone Resin 50 g of polymethylsilsesquioxane (the trade name: Tospearl 145A, manufactured by Toshiba Silicone Corporation) was placed as a silicone resin in a 100-cc kneader. Under agitation with the kneader, a mixture of 5 g of PEG-12 glyceryl laurate and 20 g of water was gradually charged for 10-min agitation while the resulting mixture remained as it was. Additionally, to the mixture thus obtained, 0.5 g of a dimethyldiallylammonium chloride-acrylamide copolymer was gradually added, for 10-min agitation. The resulting powder was taken out, heated at 100° C. for 3 hours, washed with water, and filtered and cleansed. Subsequently, the resulting mixture was dried and pulverized, to obtain the desired silicone resin with the surface hydrophilicaly treated.

Production Example 7

Production of Hydrophilicaly Treated Silicone Elastomer Powder

Dimethicone-crosslinked Elastomer 50 g of a silicone elastomer powder (the trade name: Torayfil E-506C, manufactured by Toray-Dow Corning Co., Ltd.) was placed in a 100-cc kneader. Under agitation with the kneader, a mixture of 5 g of PEG-12 glyceryl laurate, 1 g of melanosilanol triPEG-8-glyceryl cocoate and 10 g of ethanol was gradually charged for 10-min agitation while the resulting mixture remained as it was. Additionally, to the mixture thus obtained, a mixture solution of 5 g of o-[2-hydroxy-3-(trimethylammonio)propyl] chloride guar gum and 10 g of 0.001M KOH was added gradually, for 10-min agitation. The resulting powder was taken out, washed with water, and filtered and cleansed. Subsequently, the resulting mixture was dried and pulverized, to obtain the desired silicone elastomer with the surface hydrophilicaly treated.

Production Example 8

Production of Hydrophilicaly Treated Styrenedivinylbenzene Pinhole Polymer 50 g of a styrenedivinylbenzene pinhole polymer (the trade name: Styrenedivinylbenzene Pinhole Polymer 3010, manufactured by Nippon Chemical Co., Ltd.) was placed in a 100-cc kneader. Under agitation with the kneader, a mixture of 5 g of PEG-12 glyceryl laurate and 10 g of 0.001M KOH was gradually charged for 10-min agitation, while the resulting mixture remained as it was. Additionally, to the mixture thus obtained, 5 g of o-[2-hydroxy-3-(trimethylammonio) propyl] chloride guar gum was added gradually, for 20-min agitation. The resulting powder was taken out, heated at 80° C. for 10 hours, washed with water, and filtered and cleansed. Subsequently, the resulting mixture was dried and pulverized, to obtain the desired styrenedivinylbenzene pinhole polymer with the surface hydrophilicaly treated.

Production Example 9

Production of Hydrophilicaly Treated Nylon

20 Kg of nylon (the trade name: Nylon SP-500, manufactured by Toray Co., Ltd.) was placed in a 100-liter puddle mixer. Under agitation with the puddle mixer, a mixture of 1 Kg of PEG-12 glyceryl laurate, 200 g of methylsilanol triPEG-8-glyceryl cocoate and 1 Kg of ethanol was gradually charged for 20-min agitation while the resulting mixture remained as it was. Additionally, to the mixture thus obtained, 500 g of a dimethyldiallylammonium chloride-acrylamide copolymer was added gradually, for 20-min agitation. The resulting powder was taken out, heated at 100° C. for 3 hours, washed with water, and filtered and cleansed. Subsequently, the resulting mixture was dried and pulverized, to obtain the desired nylon with the surface hydrophilicaly treated.

Production Example 10

Production of Hydrophilicaly Treated Polyethylene Powder 50 g of a polyethylene powder (the trade name: Flosen OF-80, manufactured by Sumitomo Seika Chemical Co., Ltd.) was placed in a 100-cc kneader. Under agitation with the kneader, a mixture of 5 g of PEG-7 glyceryl cocoate, 2 g of methylsilanol triPEG-8-glyceryl cocoate and 20 g of ethanol was gradually charged for 10-min agitation while the resulting mixture remained as it was. Additionally, to the mixture thus obtained, a mixture solution of 5 g of o-[2-hydroxy-3-(trimethylammonio)propyl] chloride guar gum and 10 g of 0.001M KOH was added gradually, for 10-min agitation at 80° C. The resulting powder was taken out, washed with water, and filtered and cleansed. Subsequently, the resulting mixture was dried and pulverized, to obtain the desired polyethylene powder with the surface hydrophilicaly treated.

Production Example 11

Production of Hydrophilicaly Treated Lauroyl Lysine 2000 g of lauroyl lysine was placed in a 25-liter Henschel mixer. Under agitation with the Henschel mixer, a mixture of 100 g of polypropylene glycol-26 oleate and 10 g of ethanol was gradually charged for 10-min agitation, while the resulting mixture remained as it was. Additionally, to the mixture thus obtained, 20 g of o-[2-hydroxy-3-(trimethylammonio) propyl] chloride guar gum was added gradually, for 20-min agitation. The resulting powder was taken out, washed with water, and filtered and cleansed. Subsequently, the resulting mixture was dried and pulverized, to obtain the desired lauroyl lysine with the surface hydrophilicaly treated.

Comparative Production Example 1

Production of Hydrophilicaly Treated Nylon Resin 2.5 g of o-[2-hydroxy-3-(trimethylammonio)propyl]hydroxyethylcellulose chloride was added to 200 g of purified water, for uniform dissolution. To the resulting solution were added 200 g of an aqueous 1% monomethylsilanetriol lactate solution and 57 g of Nylon (the trade name: Nylon SP-500 manufactured by Toray Co., Ltd.) as a nylon type, for 16-hour treatment with a ball mill. After the treatment, the resulting slurry was taken out, washed with water and filtered and cleansed. Subsequently, the resulting mixture was dried and pulverized, to obtain the desired nylon resin with the surface hydrophilicaly treated.

Comparative Production Example 2

Production of Hydrophilicaly Treated Polystyrene 2.0 g of o-[2-hydroxy-3-(trimethylammonio)propyl]hydroxyethylcellulose chloride was added to 400 g of purified water, for uniform dispersion. To the resulting solution was added 200 g of an aqueous 1% monomethylsilanetriol lactate solution, for uniform dissolution. To the solution thus obtained was added 73 g of polystyrene (the trade name: GS-0605, manufactured by Ganz Chemical Co., Ltd.), for agitation at 60° C. for 18 hours. Then, the resulting mixture was cooled, from which the resulting slurry was taken out, washed with water, and filtered and cleansed. Subsequently, the resulting mixture was dried and pulverized, to obtain the desired polystyrene with the surface hydrophilicaly treated.

Comparative Production Example 3

Production of Hydrophilicaly Treated PMMA 2.5 g of a dimethyldiallylammonium chloride.acrylamide copolymer was added to 200 g of purified water, for uniform dispersion. To the resulting solution were added 200 g of an aqueous 1% monomethylsilanetriol lactate solution and 57 g of PMMA (the trade name: GMX-0615, manufactured by Ganz Chemical Co., Ltd.), for treatment with a ball mill for 16 hours. After the treatment, the resulting slurry was taken out, washed with water and filtered and cleansed. Subsequently, the resulting mixture was dried and pulverized, to obtain the desired PMMA with the surface hydrophilicaly treated.

Comparative Production Example 4

Production of Hydrophilicaly Treated Silicone Resin 2.5 g of a dimethyldiallylammonium chloride-acrylamide copolymer was added to 200 g of purified water, for dissolution. To the resulting solution were added 200 g of an aqueous 1% solution of methylsilanol triPEG-8-glyceryl cocoate and 73 g of polymethylsilsesquioxane (the trade name: Tospearl 145A, manufactured by Toshiba Silicone Co., Ltd.) as a silicone resin, for uniform dissolution. The solution thus obtained was retained at 50° C. under heating, for 10-hour agitation. Then, the mixture was cooled, to take out the resulting slurry, followed by washing with water, filtration and cleansing. Subsequently, the resulting mixture was dried and pulverized, to obtain the desired silicone resin with the surface hydrophilicaly treated.

Comparative Production Example 5

Production of Hydrophilicaly Treated Polyethylene Powder 2.5 g of a dimethyldiallylammonium chloride-acrylamide copolymer was dissolved in 200 g of purified water. To the resulting solution were added 200 g of an aqueous 1% solution of methylsilanol triPEG-8-glyceryl cocoate and 73 g of a polyethylene powder (the trade name: Flosen OF-80, manufactured by Sumitomo Seika Chemical Co., Ltd.) as a polyethylene, for uniform dissolution. The solution thus obtained was retained at 50° C. under heating, for 10-hour agitation. Then, the mixture was cooled, to take out the resulting slurry, followed by washing with water, filtration and cleansing. Subsequently, the resulting mixture was dried and pulverized, to obtain the desired polyethylene powder with the surface hydrophilicaly treated.

Evaluation Example 1

Individual samples were evaluated by the following Evaluation method. As the samples, herein, the hydrophilicaly treated (surface-treated) powders obtained in the Production Examples 1 through 11, the hydrophilicaly treated (surface-treated) powders obtained in the Comparative Production Examples 1 through 5 and untreated powders (the silicone resin, PMMA, nylon, polystyrene, the silicone elastomer powder, the polyethylene powder, the styrenedivinylbenzene pinhole polymer and the nylon-silica composite) were used.
(Evaluation Method)

Accurately 32 g of purified water was charged into a transparent vessel having a capacity of 50 ml. 1.0 g of the sample was added thereto, strongly filtered 40 times a day, and then allowed to stand still to evaluate the dispersed state at that time. The same procedure was repeated, and it was evaluated whether the powder was gathered (how many times the sample was strongly shaken to gather the powder (particles)) in the gas-liquid interface. The results of these evaluations are shown below in Tables 2(a), (b), (c) and (d).

TABLE 2(a)

Results of the evaluation of the dispersed states of various powders

| | | Production Example 1 | Production Example 2 | Production Example 3 | Production Example 4 | Production Example 5 |
|---|---|---|---|---|---|---|
| Surface-treating Agents | Powders Water-soluble polyalkylene glycol derivatives | nylon PEG-12 glyceryl laurate | polystyrene PEG-12 glyceryl laurate | PMMA polypropylene glycol-26 oleate | polystyrene PEG-12 glyceryl laurate | nylon polypropylene glycol-26 oleate |

TABLE 2(a)-continued

Results of the evaluation of the dispersed states of various powders

|  | Production Example 1 | Production Example 2 | Production Example 3 | Production Example 4 | Production Example 5 |
|---|---|---|---|---|---|
| Water-soluble cationic polymers | — | o-[2-Hydroxy-3-(trimethylammonio)propyl] chloride guar gum | dimethyldiallylammonium chloride•acrylamide copolymer | o-[2-Hydroxy-3-(trimethylammonio)propyl] chloride guar gum | o-[2-Hydroxy-3-(trimethylammonio)propyl] chloride guar gum |
| Low-molecular organosilicon derivatives | — | — | monomethylsilanetriol lactate | — | — |
| Alkali | — | — | — | KOH | — |
| Alcohol | — | — | — | — | ethanol |
| Heating treatment (° C.) | — | — | — | — | — |
| Shaking number (times) | 1520 | 1600 | 1600 | 1700 | 1800 |

TABLE 2(b)

Results of the evaluation of the dispersed states of various powders

|  |  | Production Example 6 | Production Example 7 | Production Example 8 |
|---|---|---|---|---|
| Powders |  | silicone resin | silicone elastomer powder | styrenedivinyl benzene pinhole polymer |
| Surface-treating Agents | Water-soluble polyalkylene glycol derivatives | PEG-12 glyceryl laurate | PEG-12 glyceryl laurate | PEG-12 glyceryl laurate |
|  | Water-soluble cationic polymers | dimethyldiallylammonium chloride•acrylamide copolymer | o-[2-Hydroxy-3-(trimethylammonio)propyl] chloride guar gum | o-[2-Hydroxy-3-(trimethylammonio)propyl] chloride guar gum |
|  | Low-molecular organosilicon derivatives | — | methylsilanol triPEG-8 glyceryl cocoate | — |
| Alkali |  | — | KOH | KOH |
| Alcohol |  | — | ethanol | — |
| Heating treatment (° C.) |  | 100 | — | 80 |
| Shaking number (times) |  | 1800 | 1900 | 1900 |

|  |  | Production Example 9 | Production Example 10 |
|---|---|---|---|
| Powders |  | nylon | polyethylene powder |
| Surface-treating Agents | Water-soluble polyalkylene glycol derivatives | PEG-12 glyceryl laurate | PEG-7 glyceryl cocoate |
|  | Water-soluble cationic polymers | dimethyldiallylammonium chloride•acrylamide copolymer | o-[2-Hydroxy-3-(trimethylammonio)propyl] chloride guar gum |
|  | Low-molecular organosilicon derivatives | methylsilanol triPEG-8 glyceryl cocoate | methylsilanol triPEG-8 glyceryl cocoate |
| Alkali |  | — | KOH |
| Alcohol |  | ethanol | ethanol |

TABLE 2(b)-continued

Results of the evaluation of the dispersed states of various powders

| | | |
|---|---|---|
| Heating treatment (° C.) | 100 | 80 |
| Shaking number (times) | 2000 | 1880 |

TABLE 2(c)

Results of the evaluation of the dispersed states of various powders

| | | Production Example 11 |
|---|---|---|
| Powders | | lauroyl lysine |
| Surface-treating Agents | Water-soluble polyalkylene glycol derivatives | polypropylene glycol-26 oleate |
| | Water-soluble cationic polymers | o-[2-Hydroxy-3-(trimethylammonio)propyl] chloride guar gum |
| | Low-molecular organosilicon derivatives | — |
| | Alkali | — |
| | Alcohol | ethanol |
| Heating treatment (° C.) | | — |
| Shaking number (times) | | 1800 |

TABLE 2(d)

Results of the evaluation of the dispersed states of various powders

| | | Comparative Production Example 1 | Comparative Production Example 2 | Comparative Production Example 3 |
|---|---|---|---|---|
| Powders | | nylon | polystyrene | PMMA |
| Surface-treating Agents | Water-soluble polyalkylene glycol derivatives | — | — | — |
| | Water-soluble cationic polymers | o-[2-Hydroxy-3-(trimethylammonio)propyl] chloride guar gum | o-[2-Hydroxy-3-(trimethylammonio)propyl] chloride guar gum | dimethyldiallylammonium chloride•acrylamide copolymer |
| | Low-molecular organosilicon derivatives | monomethylsilanetriol lactate | monomethylsilanetriol lactate | monomethylsilanetriol lactate |
| | Alkali | — | — | — |
| | Alcohol | — | — | — |
| Heating treatment (° C.) | | — | — | — |
| Shaking number (times) | | 1400 | 1340 | 1040 |

| | | Comparative Production Example 4 | Comparative Production Example 5 |
|---|---|---|---|
| Powders | | silicone resin | polyethylene powder |
| Surface-treating Agents | Water-soluble polyalkylene glycol derivatives | — | — |
| | Water-soluble cationic polymers | dimethyldiallylammonium chloride•acrylamide copolymer | dimethyldiallylammonium chloride•acrylamide copolymer |
| | Low-molecular | methylsilanol triPEG-8 | methylsilanol triPEG-8 |

TABLE 2(d)-continued

Results of the evaluation of the dispersed states of various powders

|  | organosilicon derivatives | glyceryl cocoate | glyceryl cocoate |
|---|---|---|---|
| Alkali | | — | — |
| Alcohol | | — | — |
| Heating treatment (° C.) | | — | — |
| Shaking number (times) | | 1120 | 1000 |

(Results of Evaluation)

Consequently, thus, all the surface-treated powders obtained in the Production Examples 1 through 11 were greatly dispersed even after 1500 times or more of strong shaking, absolutely without any change such as gathering of particles (agglomeration of particles) in the gas-liquid interface under observation. In case that two or more processes of the alkali addition, the alcohol addition and the heating treatment were done, the resulting surface-treated powders were greatly dispersed under shaking 1900 times or more. Particularly for the dispersion of the polyethylene powder in the Comparative Production Examples, the shaking number was the smallest, so it was determined that the hydrophilic treatment of the polyethylene powder was the most difficult. For the dispersion of the hydrophilicaly treated polyethylene powder in the Production Example 10 in accordance with the present invention, however, all the processes of the alkali addition, the alcohol addition and the heating treatment were done, so that the polyethylene powder was finely dispersed under shaking up to 1880 times, absolutely without any change such as gathering of particles (agglomeration of particles) in the gas-liquid interface. Alternatively, all the surface-treated powders obtained in the Comparative Production Examples 1 through 5 were greatly dispersed under shaking 1000 times but some particles gathered in the gas-liquid interface under strong shaking less than 1400 times. Since the powders used in the Production Examples 1 through 11 (non-surface-treated powders) were not dispersed even under strong shaking, purified water as the dispersion medium therefor was transparent.

Evaluation Example 2

The individual samples were evaluated by the following Evaluation method. As the samples, only the surface-treated powders obtained in the Production Examples 1 through 11 among the samples used in the Evaluation Example 1 were used.
(Evaluation Method)

Each of the samples was allowed to standstill at ordinary temperature for 2.5 years, at 40° C. for 6 months, and at 50° C. for 3 months, and the conditions at each time were observed. Further, after the observation, it was evaluated whether the sample was clearly re-dispersed or not, when the transparent vessel was shaken twice (ready re-dispersibility)
(Results of Evaluation)

As a result, an abnormal change such as gathering of particles or agglomeration of particles in the gas-liquid interface was not observed at all in the samples, which were allowed to stand still under the respective conditions. Also in the evaluation of the ready re-dispersibility, the samples were clearly re-dispersed, and the abnormal change such as gathering of particles or the like in the gas-liquid interface was not observed at all after allowing the samples to stand still.

Production Example 12

Production of Dispersion of Hydrophilicaly Treated Nylon 100 g of the hydrophilicaly treated nylon produced in the Production Example 9 was mixed with 100 g of purified water, for agitation with a disper for 10 minutes, to produce the desired dispersion of hydrophilicaly treated nylon.

Production Example 13

Production of Dispersion of Hydrophilicaly Treated Silicone Resin 100 g of the hydrophilicaly treated silicone resin produced in the Production Example 6 was mixed with 100 g of purified water, for agitation with a disper for 10 minutes, to produce the desired dispersion of hydrophilicaly treated silicone resin.

Example 1

Preparation (Production) of Cosmetic-1

A cosmetic (hair mascara) was prepared (produced) according to the following method based on the composition of the following Table 3.
(Preparation Method)

Components (1), (2) and (12) were dispersed in component (16). Then, a mixture obtained by previously mixing component (11) with component (13) was added to the resulting dispersion. The components (5) and (6) were added to the resulting mixture, and components (3), (4), (7), (8), (9), (10), (14) and (15) were further added thereto, and were mixed with stirring, to obtain a desired cosmetic.

It is preferable that components (4), (9) and (15) are previously swollen in water.

TABLE 3

Composition of cosmetic (hair mascara) (unit: part by weight)

| Components | Amount |
|---|---|
| (1) Iron oxide | 4.5 |
| (2) Ultramarine | 0.5 |
| (3) Iridescent pigment | 3.0 |
| (4) Bentonite | 1.0 |
| (5) Silica fine powder* | 1.0 |
| (6) Hydrophilicaly treated nylon obtained in the Production Example 1 | 6.0 |
| (7) Polyethylene glycol 200 | 6.0 |
| (8) 1,3-Butylene glycol | 4.0 |

TABLE 3-continued

Composition of cosmetic (hair mascara) (unit: part by weight)

| Components | Amount |
|---|---|
| (9) Xanthan gum | 1.0 |
| (10) Alkylacrylate copolymer emulsion | 10.0 |
| (11) brucine-modified alcohol (95%) | 10.0 |
| (12) Sodium hexametaphosphate | 0.1 |
| (13) Methylparaben | 0.3 |
| (14) perfume | 0.05 |
| (15) Carboxymethylcellulose | 0.05 |
| (16) Purified water | balance |

*Aerosil 200

Example 2

Preparation of Cosmetic-2

A cosmetic was prepared by the same method as in the Example 1, except for the use of the hydrophilicaly treated polystyrene obtained in the Production Example 2 instead of the hydrophilicaly treated nylon obtained in the Production Example 1.

Example 3

Preparation of Cosmetic-3

Except for the use of the hydrophilicaly treated PMMA obtained in the Production Example 3 instead of the hydrophilicaly treated nylon obtained in the Production Example 1, a cosmetic was prepared by the same method as in the Example 1.

Example 4

Preparation of Cosmetic-4

Except for the use of the hydrophilicaly treated polystyrene obtained in the Production Example 4 instead of the hydrophilicaly treated nylon obtained in the Production Example 1, a cosmetic was prepared by the same method as in the Example 1.

Example 5

Preparation of Cosmetic-5

Except for the use of 2.0 parts by weight of the hydrophilicaly treated nylon obtained in the Production Example 5 instead of the hydrophilicaly treated nylon obtained in the Production Example 1, a cosmetic was prepared by the same method as in the Example 1.

Example 6

Preparation of Cosmetic-6

Except for the use of the hydrophilicaly treated silicone resin obtained in the Production Example 6 instead of the hydrophilicaly treated nylon obtained in the Production Example 1, a cosmetic was prepared by the same method as in the Example 1.

Example 7

Preparation of Cosmetic-7

Except for the use of the hydrophilicaly treated silicone elastomer powder obtained in the Production Example 7 instead of the hydrophilicaly treated nylon obtained in the Production Example 1, a cosmetic was prepared by the same method as in the Example 1.

Example 8

Preparation of Cosmetic-8

Except for the use of the hydrophilicaly treated styrenedivinylbenzene pinhole polymer obtained in the Production Example 8 instead of the hydrophilicaly treated nylon obtained in the Production Example 1, a cosmetic was prepared by the same method as in the Example 1.

Example 9

C Preparation of Cosmetic-9

Except for the use of 2.0 parts by weight of the hydrophilicaly treated lauroyl lysine obtained in the Production Example 11 instead of the hydrophilicaly treated nylon obtained in the Production Example 1, a cosmetic was prepared by the same method as in the Example 1.

Comparative Example 1

Preparation of Cosmetic-10

Except for the use of untreated nylon instead of the hydrophilicaly treated nylon obtained in the Production Example 1, a cosmetic (hair mascara) was prepared by the same method as in the Example 1.

Example 10

Preparation of Cosmetic-11

A cosmetic (gel foundation) was prepared according to the following method based on the composition of the following Table 4.

(Preparation Method)

Components (6) to (11) were dispersed and dissolved in component (16). Components (1) to (5) were dispersed in the resulting mixture. Further, the other components (components (12) to (15)) were added to the resulting dispersion, and were mixed with stirring to obtain a desired cosmetic.

TABLE 4

Composition of cosmetic (gel foundation) (unit: part by weight)

| Components | Amount |
|---|---|
| (1) Talc | 2.0 |
| (2) Titanium dioxide | 5.0 |
| (3) Iron oxide | 0.6 |
| (4) Hydrated iron oxide | 1.0 |
| (5) Tri-iron tetroxide (FeO/Fe$_2$O$_3$) | 0.1 |

TABLE 4-continued

Composition of cosmetic (gel foundation) (unit: part by weight)

| Components | Amount |
| --- | --- |
| (6) Bentonite | 0.5 |
| (7) Silica fine powder* | 0.5 |
| (8) Hydrophilicaly treated polystyrene obtained in the Production Example 2 | 6.0 |
| (9) Propylene glycol | 1.0 |
| (10) 1,3-Butylene glycol | 5.0 |
| (11) Xanthan gum | 0.5 |
| (12) Polyacrylate ethyl ester emulsion | 1.0 |
| (13) Aqueous ammonia | 0.01 |
| (14) Methylparaben | 0.01 |
| (15) Perfume | 0.05 |
| (16) Purified water | balance |

*Aerosil 200

Comparative Example 2

Preparation of Cosmetic-12

Except for the use of untreated polystyrene instead of the hydrophilicaly treated polystyrene obtained in the Production Example 2, a cosmetic (gel foundation) was prepared by the same method as in the Example 10.

Example 11

Preparation of Cosmetic-13

A cosmetic (jelly pack) was prepared according to the following method based on the composition of the following Table 5.

(Preparation Method)

Components (2) to (6) were added to component (1), and subsequently, the mixture obtained was heated. Component (7) was added to the mixture obtained, to prepare a uniform solution. Component (8) was added to the resulting mixed solution, and dispersed therein. Further, a mixture obtained by previously dissolving components (10) to (13) in component (9) and a mixture obtained by previously dissolving component (14) in component (15) were added to the mixture (dispersion) obtained, and mixed therewith. Next, the resulting mixture was de-aerated, and cooled to obtain a desired cosmetic.

TABLE 5

Composition of cosmetic (jelly pack) (unit: part by weight)

| Components | Amount |
| --- | --- |
| (1) Purified water | balance |
| (2) Glycerin | 1.5 |
| (3) 1,2-Pentanediol | 1.0 |
| (4) 1,3-Butylene glycol | 1.5 |
| (5) Polyethylene glycol | 1.0 |
| (6) Polyoxypropylene (20) methy glucoside | 3.0 |
| (7) Polyvinyl alcohol | 13.5 |
| (8) Hydrophilicaly treated nylon obtained in the Production Example 5 | 10.0 |
| (9) Ethanol | 5.0 |
| (10) Methylparaben | 0.1 |
| (11) Perfume | 0.1 |
| (12) Polyoxyethylene (20) Polyoxypropylene glycol (20) | 1.5 |
| (13) Polyoxypropylene (9) Diglyceryl ether | 2.0 |
| (14) Rosemary extract | 0.2 |
| (15) Purified water | 0.9 |

Comparative Example 3

Preparation of Cosmetic-14

Except for the use of untreated nylon instead of the hydrophilicaly treated nylon obtained in the Production Example 5, a cosmetic (jelly pack) was prepared by the same method as in the Example 11.

Example 12

Preparation of Cosmetic-15

A cosmetic (jelly pack) was prepared according to the following method based on the composition of the following Table 6.

(Preparation Method)

Components (2) to (6) were added to component (1), and subsequently, the mixture obtained was heated. Component (7) was added to the mixture obtained, to prepare a uniform solution. Component (8) was added to the resulting mixed solution, and dispersed therein. Further, a mixture obtained by previously dissolving components (10) to (13) in component (9) and a mixture obtained by previously dissolving component (14) in component (15) were added to the mixture (dispersion) obtained, and mixed therewith. Next, the resulting mixture was de-aerated, and cooled to obtain a desired cosmetic.

TABLE 6

Composition of cosmetic (jelly pack) (unit: part by weight)

| Components | Amount |
| --- | --- |
| (1) Purified water | balance |
| (2) Glycerin | 1.5 |
| (3) 1,2-Pentanediol | 1.0 |
| (4) 1,3-Butylene glycol | 1.5 |
| (5) polyethylene glycol | 1.0 |
| (6) Polyoxypropylene (20) methyl glucoside | 3.0 |
| (7) Polyvinyl alcohol | 13.5 |
| (8) Hydrophilicaly treated lauroyl lysine obtained in the Production Example 11 | 10.0 |
| (9) Ethanol | 5.0 |
| (10) Methylparaben | 0.1 |
| (11) Perfume | 0.1 |
| (12) Polyoxyethylene (20) polyoxypropylene glycol (20) | 1.5 |
| (13) Polyoxypropylene (9) diglyceryl ether | 2.0 |
| (14) Rosemary extract | 0.2 |
| (15) Purified water | 0.9 |

Comparative Example 4

Preparation of Cosmetic-16

Except for the use of untreated lauroyl lysine instead of the hydrophilicaly treated lauroyl lysine obtained in the Production Example 11, a cosmetic (jelly pack) was prepared by the same method as in the Example 12.

Example 13

Preparation of Cosmetic-17

A cosmetic (carmine lotion) was prepared according to the following method based on the composition of the following Table 7.

(Preparation Method)

Components (2), (3) and (4) were added to component (1), and uniformly dissolved therein. Then, components (5) to (10) were added to the mixture obtained, and uniformly dispersed therein. Further, an ethanol solution obtained by previously dissolving components (11) and (13) in component (12) was added to the resulting dispersion, and the mixture obtained was stirred. Subsequently, components (14), (15) and (16) were added to the mixture obtained, and mixed therewith stirring, to obtain a desired cosmetic.

TABLE 7

Composition of cosmetic (carmine lotion) (unit: part by weight)

| Components | Amount |
| --- | --- |
| (1) Purified water | balance |
| (2) Propylene glycol | 5.0 |
| (3) Sodium chloride | 0.2 |
| (4) ε-Aminocaproic acid | 0.5 |
| (5) Bentonite | 0.2 |
| (6) Hydrophilicaly treated nylon obtained in the Production Example 1 | 2.5 |
| (7) Hydrophilicaly treated PMMA obtained in the Production Example 3 | 2.5 |
| (8) Talc | 0.5 |
| (9) Zinc oxide | 0.6 |
| (10) Kaolin | 0.5 |
| (11) Oxybenzene | 0.05 |
| (12) Ethanol | 7.0 |
| (13) Methylparaben | 0.2 |
| (14) Perfume | 0.2 |
| (15) Sorbitol | 1.0 |
| (16) Polyethylene glycol | 0.5 |

Comparative Example 5

Preparation of Cosmetic-18

Except for the use of untreated nylon instead of the hydrophilicaly treated nylon obtained in the Production Example 1 and for the use of untreated PMMA instead of the hydrophilicaly treated PMMA obtained in the Production Example 3, a cosmetic (carmine lotion) was prepared by the same method as in the Example 13.

Example 14

Preparation of Cosmetic-19

A cosmetic (emulsion) was prepared according to the following method based on the composition of the following Table 8.
(Preparation Method)

Components (1) to (5), (7) and (8) were dissolved through heating, and then mixed to prepare an oil phase component, and the resulting oil phase component was maintained at 80° C. Meanwhile, components (9) to (16) were dissolved in component (19), and subsequently, components (17) and (18) were further added to the mixture obtained, and uniformly dispersed therein. The resulting mixture was maintained at 80° C. to form an aqueous (water) phase component. The above aqueous phase component was added to the above oil phase component for emulsification. After the emulsion was cooled, component (6) was added to the emulsion to obtain a desired cosmetic. Also, the appearance of the resulting cosmetic was semi-transparent.

TABLE 8

Composition of cosmetic (emulsion) (unit: part by weight)

| Components | Amount |
| --- | --- |
| (1) Liquid paraffin | 1.0 |
| (2) Diethoxyethyl succinate | 8.0 |
| (3) Glyceryl tri-2-ethylhexanoate | 1.0 |
| (4) Cetyl isooctanoate | 1.0 |
| (5) Octamethylcyclotetrasiloxane | 1.0 |
| (6) Perfume | 0.2 |
| (7) Butylparaben | 0.1 |
| (8) Propylparaben | 0.1 |
| (9) Glycerin | 4.5 |
| (10) Ethanol | 3.0 |
| (11) Alkyl-modified carboxyvinyl polymer | 0.2 |
| (12) Potassium hydroxide | 0.1 |
| (13) Cornstarch | 2.5 |
| (14) L-Arginine L-aspartate salt | 0.01 |
| (15) Succinic acid | 0.01 |
| (16) Sodium succinate | 0.09 |
| (17) Hydrophilicaly treated polystyrene obtained in the Production Example 2 | 1.0 |
| (18) Hydrophilicaly treated PMMA obtained in the Production Example 3 | 2.0 |
| (19) Purified water | balance |

Comparative Example 6

Preparation of Cosmetic-20

Untreated polystyrene was used instead of the hydrophilicaly treated polystyrene obtained in the Production Example 2, while untreated PMMA was used instead of the hydrophilicaly treated PMMA obtained in the Production Example 3. Components (1) to (5), (7) and (8) were dissolved through heating, and subsequently, components (17) and (18) were further added to the mixture obtained, and uniformly dispersed therein, and then mixed to prepare an oil phase component. The resulting oil phase component was maintained at 80° C. Meanwhile, components (9) to (16) were dissolved in component (19), and subsequently, the resulting mixture was maintained at 80° C. to form an aqueous (water) phase component. The above aqueous phase component was added to the above oil phase component for emulsification. After the emulsion was cooled, component (6) was added to the emulsion to obtain a desired cosmetic. Also, the appearance of the resulting cosmetic was white.

Example 15

Preparation of Cosmetic-21

A cosmetic (pre-shave lotion) was prepared according to the following method based on the composition of the following Table 9.
(Preparation Method)

Components (1) to (6) were uniformly mixed together. Also, the appearance of the resulting cosmetic was semi-transparent.

TABLE 9

Composition of cosmetic (pre-shave lotion) (unit: part by weight)

| Components | Amount |
| --- | --- |
| (1) Ethanol | 94.0 |
| (2) Hydrophilicaly treated silicone resin obtained in the Production Example 6 | 4.0 |

TABLE 9-continued

Composition of cosmetic (pre-shave lotion) (unit: part by weight)

| Components | Amount |
| --- | --- |
| (3) Tri-2-ethylhexanoate glyceryl ester | 1.0 |
| (4) 1,3-Butylene glycol | 1.0 |
| (5) Tocopherol acetate | appropriate amount |
| (6) Perfume | appropriate amount |

Comparative Example 7

Preparation of Cosmetic-22

Except for the use of untreated silicone resin instead of the hydrophilicaly treated silicone resin obtained in the Production Example 6, a cosmetic (pre-shave lotion) was prepared by the same method as in the Example 15. Also, the appearance of the resulting cosmetic was white.

Example 16

Preparation of Cosmetic-23

A cosmetic (powder foundation) was prepared according to the following method based on the composition of the following Table 10.

(Preparation Method)

Components (1) to (7) were uniformly mixed and then pulverized to prepare a powdery component. Meanwhile, components (8) and (9) were dissolved through heating at 70 to 80° C., and subsequently, component (12) was added to the mixture obtained, to prepare an oil phase component. The above powdery component, the above oil phase component and components (10) and (11) were mixed using a powder mixer, to subject to treatment with a pulverizer. The resulting powder was filtered through a sieve, to remove extraneous matters. Subsequently, the powder was subjected to compression forming, to prepare a powder foundation.

TABLE 10

Composition of cosmetic (powder foundation) (unit: part by weight)

| Components | Amount |
| --- | --- |
| (1) Silicone-treated mica | 30.0 |
| (2) Silicone-treated talc | 20.0 |
| (3) Silicone-treated titanium dioxide | 10.0 |
| (4) Silicone-treated yellow iron oxide | 4.0 |
| (5) Silicone-treated red oxide | 2.0 |
| (6) Silicone-treated black iron oxide | 0.2 |
| (7) Hydrophilicaly treated nylon obtained in the Production Example 5 | 10.0 |
| (8) Vaseline | 11.5 |
| (9) Fluid paraffin | 9.0 |
| (10) Purified water | 2.0 |
| (11) 1,3-Butylene glycol | 1.0 |
| (12) Perfume | appropriate amount |

Comparative Example 8

Preparation of Cosmetic-24

Except for the use of untreated nylon instead of the hydrophilicaly treated nylon obtained in the Production Example 5, a cosmetic (powder foundation) was prepared by the same method as in the Example 16.

Example 17

Preparation of Cosmetic-25

A cosmetic (lipstick) was prepared according to the following method based on the composition of the following Table 11.

(Preparation Method)

Components (1) to (7) were uniformly mixed through heating to 80° C., to prepare an oil phase component. Next, components (8) to (12) were uniformly mixed together, to prepare a powdery component. Using a three-roll, the above oil phase component and the above powdery component were kneaded together several times, followed by degassing. The resulting mixture was put into a mold, followed by cooling for solidification, to prepare a lipstick.

TABLE 11

Composition of cosmetic (lipstick) (unit: part by weight)

| Components | Amount |
| --- | --- |
| (1) Isodecyl isononanoate | 25.0 |
| (2) Fluid paraffin | 22.0 |
| (3) Ceresin wax | 10.0 |
| (4) Liquid lanoline | 10.0 |
| (5) Paraffin wax | 8.0 |
| (6) Decamethylcyclopentane siloxane | 5.0 |
| (7) Candelilla wax | 2.0 |
| (8) Hydrophilicaly treated silicone resin obtained in the Production Example 6 | 11.0 |
| (9) Yellow 4 Al lake | 2.0 |
| (10) Titanium dioxide | 2.0 |
| (11) Red 201 | 2.0 |
| (12) Red 202 | 1.0 |

Comparative Example 9

Preparation of Cosmetic-26

Except for the use of untreated silicone resin instead of the hydrophilicaly treated silicone resin obtained in the Production Example 6, a cosmetic (lipstick) was prepared by the same method as in the Example 17.

Example 18

Preparation of Cosmetic-27

A cosmetic (shampoo) was prepared according to the following method based on the composition of the following Table 12.

(Preparation Method)

Components (1) to (6) and (11) were mixed together were with stirring at 40° C., followed by heating to 80° C. To the mixture thus obtained, component (7) was added for solubilization. Subsequently, the resulting mixture was cooled to 50° C. Component (8) previously dispersed in (11) for swelling was added to the resulting mixture, followed by final addition of components (9) and (10), to prepare a shampoo.

TABLE 12

Composition of cosmetic (shampoo) (unit: part by weight)

| Components | Amount |
|---|---|
| (1) Polyoxyethylene lauryl ether disodium sulfosuccinate | 15.0 |
| (2) Propylbetaine amide | 5.0 |
| (3) C8-C12 alkyl glucoside (with added 2 moles of sugar chains) | 2.0 |
| (4) Diethanolamide laurate | 2.0 |
| (6) Hydrophilicaly treated silicone resin obtained in the Production Example 6 | 2.0 |
| (7) Highly polymerized dimethylpolysiloxane (20,000,000 cs) | 2.0 |
| (8) Dimethylpolysiloxane (200 cs) | 1.0 |
| (9) Polyoxyethylene lauryl ether (E.O. = 20) | 0.5 |
| (10) Polyoxyethylene lauryl ether (E.O. = 4) | 0.3 |
| (11) Purified water | balance. |

Comparative Example 10

Preparation of Cosmetic-28

Except for the use of untreated silicone resin instead of the hydrophilicaly treated silicone resin obtained in the Production Example 6, a cosmetic (shampoo) was prepared by the same method as in the Example 18.

Example 19

Preparation of Cosmetic-29

A cosmetic (body shampoo) was prepared according to the following method based on the composition of the following Table 13.
(Preparation Method)
Components (1) to (5) were added to component (6), and the mixture obtained was stirred to prepare a body shampoo.

TABLE 13

Composition of cosmetic (body shampoo) (unit: part by weight)

| Components | Amount |
|---|---|
| (1) Triethanolamine laurate | 30.0 |
| (2) Lauryldimethylaminoacetate betaine | 5.0 |
| (3) Glycerin | 5.0 |
| (4) Edetate salt | 5.0 |
| (5) Hydrophilicaly treated PMMA obtained in the Production Example 3 | 3.0 |
| (6) Purified water | balance. |

Comparative Example 11

Preparation of Cosmetic-30

Except for the use of untreated PMMA instead of the hydrophilicaly treated PMMA obtained in the Production Example 3, a cosmetic (body shampoo) was prepared by the same method as in the Example 19.

Example 20

Preparation of Cosmetic-31

A cosmetic (soap) was prepared according to the following method based on the composition of the following Table 14.

(Preparation Method)
Components (1) to (4) were added to component (5), to prepare a soap.

TABLE 14

Composition of cosmetic (soap) (unit: part by weight)

| Components | Amount |
|---|---|
| (1) Hydrophilicaly treated nylon obtained in the Production Example 9 | 5.0 |
| (2) Coconut oil • tallow fatty acid sodium salt | 82.0 |
| (3) Dibutylhydroxytoluene | 0.1 |
| (4) Cetanol | 5.0 |
| (5) Purified water | balance. |

Comparative Example 12

Preparation of Cosmetic-32

Except for the use of untreated nylon instead of the hydrophilicaly treated nylon obtained in the Production Example 9, a cosmetic (soap) was prepared by the same method as in the Example 20.

Example 21

Preparation of Cosmetic-33

A cosmetic (O/W liquid foundation) was prepared according to the following method based on the composition of the following Table 15.
(Preparation Method)
Components (1) to (6) were mixed together, and dissolved through heating at 80° C., to prepare an oil phase component. Meanwhile, component (17) was heated to 70° C., to which (8) was added for swelling. Component (7) previously dispersed in component (9) was added to the resulting mixture, for dissolution. Further, components (10) and (11) were added to the resulting mixture for dissolution. Then, components (12) to (16) were dispersed in the resulting solution with stirring, to prepare in an aqueous phase component. The above oil phase component was added to the above aqueous phase component with stirring, and dispersed with Homo-Mixer for emulsification. Subsequently, the emulsion thus obtained was cooled to room temperature, to prepare an O/W liquid foundation.

TABLE 15

Composition of cosmetic (O/W liquid foundation) (unit: part by weight)

| Components | Amount |
|---|---|
| (1) Stearic acid | 2.4 |
| (2) Propylene glycol monostearate | 2.0 |
| (3) Setostearyl alcohol | 0.2 |
| (4) Liquid lanoline | 2.0 |
| (5) Fluid paraffin | 3.0 |
| (6) Isopropyl myristate | 8.5 |
| (7) Sodium carboxymethylcellulose | 0.2 |
| (8) Bentonite | 0.5 |
| (9) Dipropylene glycol | 4.0 |
| (10) Triethanolamine | 1.1 |
| (11) Methylparaben | 0.2 |
| (12) Titanium dioxide | 8.0 |
| (13) Hydrophilicaly treated nylon obtained in the Production Example 9 | 4.0 |
| (14) Iron oxide | 0.6 |
| (15) Hydrated iron oxide | 1.0 |

TABLE 15-continued

Composition of cosmetic (O/W liquid foundation) (unit: part by weight)

| Components | Amount |
|---|---|
| (16) Tri-iron tetroxide (FeO•Fe$_2$O$_3$) | 0.1 |
| (17) Purified water | balance. |

Example 22

Preparation of Cosmetic-34

Except for the use of the hydrophilicaly treated nylon dispersion obtained in the Production Example 12 as adjusted to 8% (4% as the powdery component) instead of the hydrophilicaly treated nylon obtained in the Production Example 9, a cosmetic (O/W liquid foundation) was prepared by the same method as in the Example 21.

Comparative Example 13

Preparation of Cosmetic-35

Except for the use of untreated nylon instead of the hydrophilicaly treated nylon obtained in the Production Example 9, a cosmetic (O/W liquid foundation) was prepared by the same method as in the Example 21.

Example 23

Preparation of Cosmetic-36

A cosmetic (aqueous nail enamel) was prepared according to the following method based on the composition of the following Table 16.

(Preparation Method)

Components (1) to (3) were mixed together with stirring, and the mixture thus obtained was added to the components (4) to (10) which were mixed together separately with stirring, for mixing and dispersion, to prepare an aqueous nail enamel.

TABLE 16

Composition of cosmetic (aqueous nail enamel) (unit: part by weight)

| Components | Amount |
|---|---|
| (1) Red 226 | 1.0 |
| (2) Red iron oxide | 3.0 |
| (3) Hydrophilicaly treated PMMA obtained in the Production Example 3 | 2.0 |
| (2) Silicone-based defoaming agent | 0.1 |
| (4) Polyoxyethylene nonylphenyl ether | 0.2 |
| (5) Hydroxyethylcellulose | 0.2 |
| (6) Acryl polymer emulsion (the polymer at 45 wt %) | 75.0 |
| (7) Dibutyl phthalate | 3.0 |
| (8) Diethylene glycol monoethyl ether | 4.0 |
| (9) Methylparaben | 0.1 |
| (10) Purified water | balance. |

Comparative Example 14

Preparation of Cosmetic-37

Except for the use of untreated PMMA instead of the hydrophilicaly treated PMMA obtained in the Production Example 3, a cosmetic (aqueous nail enamel) was prepared by the same method as in the Example 23.

Example 24

Preparation of Cosmetic-38

A cosmetic (sunscreen cream) was prepared according to the following method based on the composition of the following Table 17.

(Preparation Method)

Components (1) to (10) were dissolved through heating to 70° C., to prepare an oil phase component. Meanwhile, the components (11) to (16) were dissolved through heating to 70° C., to prepare an aqueous phase component. The above oil phase component was added to the above aqueous phase component. The particles in the resulting emulsion were homogenized using a Homo-Mixer. The emulsion thus obtained was subjected to deairing, filtration and cooling, to prepare a sunscreen cream.

TABLE 17

Composition of cosmetic (sunscreen cream) (unit: part by weight)

| Components | Amount |
|---|---|
| (1) 2-Ethylhexyl p-methoxycinnamate | 5.0 |
| (2) 4-t-Butyl-4'-methoxydibenzoylmethane | 1.0 |
| (3) Squalene | 10.0 |
| (4) Vaseline | 5.0 |
| (5) Stearyl alcohol | 3.0 |
| (6) Stearic acid | 3.0 |
| (7) Glyceryl monostearate | 3.0 |
| (8) Ethyl polyacrylate | 1.0 |
| (9) Antioxidant | appropriate amount |
| (10) Preservative | appropriate amount |
| (11) Dipropylene glycol | 7.0 |
| (12) Titanium dioxide (surface-treated with alumina) | 5.0 |
| (13) Disodium edetate | 0.05 |
| (14) Hydrophilicaly treated silicone resin obtained in the Production Example 6 | 2.0 |
| (15) Triethanolamine 99% | 1.0 |
| (16) Purified water | balance. |

Example 25

Preparation of Cosmetic-39

Except for the use of the hydrophilicaly treated silicone resin dispersion obtained in the Production Example 13 as adjusted to 4% (2% as the powdery component) instead of the hydrophilicaly treated silicone resin obtained in the Production Example 6, a cosmetic (sunscreen cream) was prepared by the same method as in the Example 24.

Comparative Example 15

Preparation of Cosmetic-40

Except for the use of untreated silicone resin instead of the hydrophilicaly treated silicone resin obtained in the Production Example 6, a cosmetic (sunscreen cream) was prepared by the same method as in the Example 24.

Example 26

Comparative Evaluation Between the Cosmetics Obtained in the Individual Examples and the Cosmetics Obtained in the Comparative Examples The individual cosmetics obtained in the Examples and the Comparative Examples were evaluated.
(Evaluation Methods and Evaluation Results)
(1) Hair Mascara In the cosmetics of the present invention (hair mascaras obtained in Examples 1 to 9), the dispersed state of any of hydrophilicaly treated nylon, the hydrophilicaly treated polystyrene, the hydrophilicaly treated PMMA, the hydrophilicaly treated silicone resin, the hydrophilicaly treated silicone elastomer powder, the hydrophilicaly treated styrenedivinylbenzene pinhole polymer and the hydrophilicaly treated lauroyl lysine was good, and the change with lapse of time thereof was not observed under each conditions of 0° C., 5° C., 10° C., 20° C., 40° C. and an aging condition of 0 to 40° C. The dispersed state of the pigments (iron oxide, ultramarine, iridescent pigment and bentonite) was good without tackiness, the adhesion to the skin was even, and a feeling of dewy moist touch with a smooth spread were provided. Among the hair mascaras obtained in Examples 1 to 9, the hair mascara obtained in Example 8, namely the hair mascara produced using the hydrophilicaly treated styrenedivinylbenzene pinhole polymer was especially excellent in these effects. Meanwhile, in the hair mascara obtained in Comparative Example 1, the nylon as the pigment was liable to be floated. As a result, a rough feeling occurred, and the feeling was bad.

(2) Gel Foundation

In the cosmetic of the present invention (gel foundation obtained in Example 10), the state of the sample after storage at 40° C. for 3 months was evaluated by visual observation. Consequently, the stability with lapse of time was excellent. Also in the results of observation with an optical microscope, the dispersed state thereof was good. With respect to the smooth feeling, a new touch was provided with a residual moist touch despite a cool feeling. Regarding long wear, the touch immediately after application was maintained, and the uniform makeup film was provided with a natural finish. Meanwhile, in the gel foundation obtained in Comparative Example 2, the propensity of agglomeration of polystyrene was notably observed. As a result, polystyrene agglomerated by an external force in application on the skin were dispersed in the agglomerated state, so that a clear difference in hue (color phase) was observed between appearance color and application color.

(3) Jelly Pack

In the cosmetic of the present invention (jelly pack obtained in Example 11), hydrophilicaly treated nylon (particles) was dispersed quite well, and smoothly extended during application. The persistence of the dispersion effect was good, and the cosmetic was stable after 2 months at 50° C. With respect to the smooth feeling, the moist touch of skin was considerably provided after peeling the film. Meanwhile, in the jelly pack obtained in Comparative Example 3, nylon (particles) was agglomerated (aggregated), and not uniformly dispersed. Consequently, a rough feeling was given to the skin in applying thereon. An uncomfortable feeling was imparted much to the skin, or non-uniformity of the applied film (makeup film) was clearly observed.

In the cosmetic of the present invention (jelly pack obtained in Example 12), hydrophilicaly treated lauroyl lysine (particles) was also dispersed quite well, and smoothly extended during application. The persistence of the dispersion effect was good, and the cosmetic was stable after 2 months at 50° C. With respect to the smooth feeling, the moist touch of skin was considerably provided after peeling the film. Meanwhile, in the jelly pack obtained in Comparative Example 3, lauroyl lysine (particles) was agglomerated (aggregated), and not uniformly dispersed. Consequently, a rough feeling was given to the skin in applying thereon. An uncomfortable feeling was imparted much to the skin, or non-uniformity of the applied film (makeup film) was clearly observed.

(4) Carmine Lotion

In the cosmetic of the present invention (suncum lotion obtained in Example 13), the dispersed state of the pigments (talc, zinc oxide, kaolin, and bentonite) was quite good, and the pigments were easily (readily) re-dispersed by shaking upon use. In the observation with lapse of time at 40° C. for 3 months, the precipitation rate and the precipitation volume of the powder (pigments (talc, zinc oxide, kaolin, and bentonite) were approximately the same as the values of standard characteristics. With regard to touch, there was no slimy feeling, and an draw rate and an draw intention were appropriate. With respect to smooth feeling after application, there was no tackiness, and a moist touch and a cool feeling were also good. Meanwhile, the carmine lotion obtained in Comparative Example 5, the pigments were liable to be turned a hard cake, and re-dispersion was therefore difficult.

(5) Emulsion

In the cosmetic of the present invention (emulsion obtained in Example 14), the dispersed state of hydrophilicaly treated polystyrene (particles) and hydrophilicaly treated PMMA (particles) was good. The fineness was unchanged over the course of time at temperatures of 20° C., 40° C., 5° C. and 0° C. The application feeling was light and soft, with a smooth feeling on the skin. With respect to the feeling after application, the affinity for the skin, the smoothness of the skin, and a moist feeling on the skin, without any feeling of tackiness were given, and the whiteness of the powder itself was not noticeable. Meanwhile, in the emulsion obtained in Comparative Example 6, the agglomerated particles of polystyrene and PMMA were much observed. Consequently, the rough feeling was provided, and both of the smooth feeling and the smooth feeling after application were bad.

(6) Pre-shave Lotion

In the cosmetic of the present invention (the pre-shave lotion obtained in the Example 15), the dispersion state of the hydrophilicaly treated silicone resin (particle) was good without any occurrence of swelling or secondary agglomeration of the silicone resin. The silicone resin was uniformly re-dispersed, under simple shaking before use. As to the smooth feeling, the blending of the silicone resin could improve the sliding property with electric shavers. Meanwhile, in the pre-shave lotion obtained in the Comparative Example 7, the silicone resin caused precipitation to induce caking, and re-dispersion was therefore impossible even by shaking.

(7) Powder Foundation

In the cosmetic of the present invention (the powder foundation obtained in Example 16), no agglomeration of the resulting treated pigments occurred. The cosmetic had excellent extension on skin, affixture to the skin and affinity for the skin. With respect to the smooth feeling, a new touch was provided with a residual moist touch despite a cool feeling. Meanwhile, in the powder foundation obtained in Comparative Example 8, the resulting color was dark. With regard to smooth feeling, there was a hard feeling to skin, but not a soft feeling. In addition, affixture of a powder contained in cosmetics to the skin is worsened, and adhesion of a cosmetic film on the skin is deficient.

(8) Lipstick

The cosmetic of the present invention (the lipstick obtained in the Example 17) was observed with an optical microscope. Consequently, the dispersion state thereof was good. With regard to smooth feeling, there was a cool feeling, and a uniform and good finish was provided. The hydrophilicaly treated silicone resin obtained in the Production Example 6 exerted an anchor effect, so that the cosmetic showed a great transfer-preventing effect (lusting property), with extremely less transfer, fading or blurring of the lipstick color with lapse of time, so that the cosmetic had excellent persistence of the cosmetic effect, namely long wear. Meanwhile, the lipstick obtained in the Comparative Example 9 caused blurring after coating on lip, involving color fading and poor long wear.

(9) Shampoo

Approximately 2 g of the inventive product (the shampoo obtained in the Example 18) or the comparative product (the shampoo obtained in the Comparative Example 10) was applied to a hair bundle (of a weight of approximately 30 g and a length of approximately 25 cm) prepared from human hair, for the evaluation of the shampoos. The applied hairs were washed and rinsed, followed by sufficiently wiping off water with a towel and drying with a dryer, to make the evaluation of the touch of the resulting hairs. Consequently, the cosmetic of the invention (the shampoo obtained in the Example 18) had great hair lubrication, smoothness under finger movement, gentleness with fluidity, and smoothness. Meanwhile, the shampoo obtained in the Comparative Example 10 was poor in view of hair lubrication, smoothness under finger movement, gentleness with fluidity, and smoothness.

(10) Body Shampoo

The cosmetic of the present invention (the body shampoo obtained in the Example 19) had good smooth feeling, with gentleness with fluidity and smoothness, without any skin irritability. When stored in a high-temperature tank at 40° C. for 3 months, further, the cosmetic was highly stable. Meanwhile, the body shampoo obtained in the Comparative Example 11 had poor smooth feeling in spite of less skin irritability and had insufficient stability.

(11) Soap

The cosmetic of the present invention (the soap obtained in the Example 20) had smoothness, good smooth feeling and washability. Meanwhile, the soap obtained in the Comparative Example 12 had poor smooth feeling, without smoothness. However, the soap had good washability.

(12) O/W Liquid Foundation

In the cosmetic of the present invention (the O/W liquid foundation obtained in the Example 21), the dispersed state of hydrophilicaly treated nylon (particles) was good under observation with an optical microscope. The change with lapse of time thereof was not observed at each temperatures of 20° C., 40° C., 5° C. and 0° C. The application feeling was light and soft, with a smooth feeling on the skin. With respect to the feeling after application, the affinity for the skin, the smoothness of the skin, and a moist feeling on the skin, without any feeling of tackiness were given. Regarding long wear, the touch immediately after application was maintained, and the uniform makeup film was provided with a natural finish. Because the O/W liquid foundation obtained in the Example 22 was produced without any powder scattering at the production process, the handleability thereof was so high that labors required for agitating the powders was not more than half of the labors in the related art. The dispersion state thereof was better than the dispersion state of the O/W liquid foundation obtained in the Example 21, so that the affinity for the skin, the smoothness of the skin, and a moist feeling on the skin, without any feeling of tackiness were given. Regarding long wear, the touch immediately after application was maintained, and the uniform makeup film was provided with a natural finish. Meanwhile, under visual observation, in the O/W liquid foundation obtained in Comparative Example 13, the agglomerated nylon particles were much observed, so that the dispersion state thereof could not be persisted. Consequently, the rough feeling was provided, and both of the smooth feeling and the smooth feeling were bad.

(13) Aqueous Nail Enamel

In the cosmetic of the present invention (the aqueous nail enamel obtained in the Example 23), the state of the sample after storage at 40° C. for 3 months was evaluated by visual observation. Consequently, the stability with lapse of time was excellent. The aqueous nail enamel had an ability of forming a stronger film and had good removability with removers. Thus, the aqueous nail enamel had good usability. Meanwhile, the aqueous nail enamel obtained in the Comparative Example 14 had poor dispersibility, so that the nail enamel caused blurring, with no formation of any stronger film.

(14) Sunscreen Cream

In the cosmetic of the present invention (the sunscreen cream obtained in the Example 24), the dispersed state of hydrophilicaly treated silicone was good. The state of the sample after storage at 40° C. for 3 months was evaluated by visual observation. Consequently, the stability with lapse of time was excellent. The application feeling was smooth, with a soft touch and an extension on skin. With respect to the feeling after application, the affinity for the skin, the smoothness of the skin, and a moist feeling on the skin, without any feeling of tackiness were given, and the whiteness of the powder itself was not noticeable. Because the sunscreen cream obtained in the Example 25 was produced without any powder scattering at the production process, the handleability thereof was so high that labors required for agitating the powders was less than half of the labors in the related art. The dispersion state thereof was better than the dispersion state of the sunscreen cream obtained in the Example 24, so that the affinity for the skin, the smoothness of the skin, and a moist feeling on the skin, without any feeling of tackiness were given. Meanwhile, in the sunscreen cream obtained in Comparative Example 15, the agglomerated silicone resin particles were much observed. Consequently, the rough feeling was provided, and both of the smooth feeling and the smooth feeling after application were bad.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

The invention claimed is:

1. A hydrophilized surface-treated powder prepared by coating the surface of a powder comprising a silicone resin and/or an organic powder with a hydrophilizing agent by its adsorption onto the surface of the powder, wherein the hydrophilizing agent contains a water-soluble polyoxyalkylene glycol derivative, a water-soluble cationic polymer and at least one low-molecular organosilicon derivative selected from dimethylsilanediol hyaluronate, monomethylsilanetriol lactate, methylsilanol mannuronate, and methylsilanol triPEG-8-glyceryl cocoate and the organic powder is at least one selected from PMMA, nylon, polyester, polystyrene, cellulose, silicone elastomer powder, silicone rubber powder, benzoguanamine, ethylene tetrafluoride, polyethylene powder, polypropylene powder, polyurethane powder, metal soap powder, starch powder, N-acylated lysine, an organic pigment, and a composite of at least one of these organic powders described above with a metal oxide and/or a metal hydroxide.

2. The hydrophilized surface-treated powder according to claim 1, wherein the particle diameter of the particle of the powder comprising the silicone resin and/or the organic powder is 0.01 to 100 μm as the mean particle diameter.

3. The hydrophilized surface-treated powder according to claim 1, wherein the surface of the particle of the powder comprising the silicone resin and/or the organic powder is coated with the hydrophilizing agent to 0.01 to 50% by weight of the surface of the particle of the powder comprising the silicone resin and/or the organic powder.

4. The hydrophilized surface-treated powder according to claim 1, wherein the silicone resin is polymethylsilsesquioxane.

5. The hydrophilized surface-treated powder according to claim 1, wherein the water-soluble polyoxyalkylene glycol derivative is at least one of polyoxyethylene monoester, polypropylene glycol monoester, polyoxyethylene glyceryl fatty acid, and polyoxyethylene glyceryl isostearate.

6. The hydrophilized surface-treated powder according to claim 1, wherein the water-soluble cationic polymer is at least one of dimethyldiallylammonium chloride-acrylamide copolymer, polydimethylmethylene piperidinium chloride, and o-[2-hydroxy-3-(trimethylammonio)propyl]hydroxyethylcellulose chloride.

7. A dispersion containing the hydrophilized surface-treated powder according to claim 1.

8. A cosmetic containing the hydrophilized surface-treated powder according to claim 1.

9. The cosmetic according to claim 8, which is any one of a rinsing cosmetic, a skin-care cosmetic, a make-up cosmetic, a hair cosmetic, a deodorant product, a dental paste, a bath agent, an aromatic product, an anti-perspiration cosmetic, and a cosmetic for ultraviolet protection.

10. The cosmetic according to claim 8, which is any one of aqueous products, emulsified products, oily products, powdery products, aerosol products, solid products, and tablet products.

* * * * *